US009339659B2

(12) United States Patent
Carbunaru et al.

(10) Patent No.: US 9,339,659 B2
(45) Date of Patent: May 17, 2016

(54) EFFICIENT EXTERNAL CHARGER FOR CHARGING A PLURALITY OF IMPLANTABLE MEDICAL DEVICES

(71) Applicant: Boston Scientific Neuromodulation Corporation, Valencia, CA (US)

(72) Inventors: Rafael Carbunaru, Valley Village, CA (US); Jordi Parramon, Valencia, CA (US); Robert Ozawa, Woodland Hills, CA (US); Jess Shi, Northridge, CA (US); Joey Chen, Valencia, CA (US); Md. Mizanur Rahman, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 31 days.

(21) Appl. No.: 14/216,956

(22) Filed: Mar. 17, 2014

(65) Prior Publication Data

US 2014/0200631 A1 Jul. 17, 2014

Related U.S. Application Data

(63) Continuation of application No. 12/624,162, filed on Nov. 23, 2009, now Pat. No. 8,676,318.

(51) Int. Cl.
*A61N 1/37* (2006.01)
*A61N 1/378* (2006.01)
*A61N 1/372* (2006.01)

(52) U.S. Cl.
CPC ........... *A61N 1/3787* (2013.01); *A61N 1/37223* (2013.01); *A61N 1/37288* (2013.01)

(58) Field of Classification Search
CPC .......... H03F 1/3247; H03F 2201/3233; A61N 1/3787
See application file for complete search history.

(56) References Cited

U.S. PATENT DOCUMENTS

| | | | | |
|---|---|---|---|---|
| 5,576,609 | A * | 11/1996 | Brown et al. | 320/164 |
| 7,127,078 | B2 | 10/2006 | Mann et al. | |
| 7,200,504 | B1 | 4/2007 | Fister | |
| 7,209,792 | B1 | 4/2007 | Parramon et al. | |
| 7,286,880 | B2 | 10/2007 | Olson et al. | |
| 8,214,042 | B2 | 7/2012 | Ozawa et al. | |
| 8,304,935 | B2 | 11/2012 | Karalis et al. | |

(Continued)

FOREIGN PATENT DOCUMENTS

| | | |
|---|---|---|
| EP | 1598092 | 11/2005 |
| WO | 2008/048321 | 4/2008 |

*Primary Examiner* — Christopher D Koharski
*Assistant Examiner* — Natasha Patel
(74) *Attorney, Agent, or Firm* — Lewis, Reese & Nesmith, PLLC

(57) ABSTRACT

An external charger for a battery in an implantable medical device (implant), and technique for charging batteries in multiple implants using such improved external charger, is disclosed. During charging, values for a parameter measured in the implants are reported from the implants to the external charger. The external charger infers from the magnitudes of the parameters which of the implants has the highest (hot) and lowest (cold) coupling to the external charger. The intensity of the magnetic charging field is optimized for the cold implant to ensure that it is charged with a maximum (fastest) battery charging current. The duty cycle of the magnetic charging field is also optimized for the hot implant to ensure that it does not exceed a power dissipation limit. As a result, charging is optimized to be fast for all of the implants, while still safe from a tissue heating perspective.

33 Claims, 18 Drawing Sheets

(56) References Cited

U.S. PATENT DOCUMENTS

| | | | |
|---|---|---|---|
| 8,321,029 | B2 | 11/2012 | Aghassian |
| 2003/0078634 | A1 | 4/2003 | Schulman et al. |
| 2004/0098068 | A1 | 5/2004 | Carbunaru et al. |
| 2006/0140139 | A1 | 6/2006 | DiSilvestro et al. |
| 2006/0149340 | A1 | 7/2006 | Karunasiri |
| 2007/0060980 | A1 | 3/2007 | Strother et al. |
| 2007/0182367 | A1 * | 8/2007 | Partovi .......................... 320/108 |
| 2008/0303480 | A1 | 12/2008 | Prutchi et al. |
| 2009/0112291 | A1 | 4/2009 | Wahlstrand et al. |
| 2010/0114216 | A1 | 5/2010 | Krause et al. |
| 2011/0087307 | A1 | 4/2011 | Carbunaru et al. |

* cited by examiner

Vbat(oc) = 3.1V:

| Iprim(rms) | Vcoil(rms) | Isec(rms) | Icap(rms) | Ibat | Vbat | Vna | Vnab = Vna - Vbat |
|---|---|---|---|---|---|---|---|
| 200 mA | 2.694 V | 25.797 mA | 25.359 mA | 1.524 mA | 3.106 V | 3.136 V | 0.030 V |
| 400 | 3.227 | 34.339 | 31.711 | 5.538 | 3.122 | 3.231 | 0.109 |
| 600 | 3.626 | 43.201 | 36.651 | 9.715 | 3.139 | 3.320 | 0.181 |
| 800 | 3.961 | 49.971 | 40.972 | 14.005 | 3.156 | 3.399 | 0.243 |
| 1000 | 4.261 | 57.500 | 44.971 | 18.382 | 3.174 | 3.467 | 0.293 |
| 1100 | 4.403 | 61.252 | 46.837 | 20.596 | 3.182 | 3.501 | 0.319 |
| 1150 | 4.523 | 63.510 | 48.258 | 21.627 | 3.187 | 3.588 | 0.401 |
| 1200 | 4.695 | 66.160 | 50.169 | 22.604 | 3.190 | 3.734 | 0.544 |
| 1250 | 4.904 | 68.984 | 52.350 | 23.482 | 3.194 | 3.916 | 0.722 |
| 1300 | 5.141 | 72.026 | 54.804 | 24.325 | 3.197 | 4.132 | 0.935 |
| 1500 | 6.210 | 85.074 | 65.800 | 27.363 | 3.210 | 5.145 | 1.935 |

Vbat(oc) = 3.1V:

| **P145** | **P147** | **P162** | **P164** | **P170** | **Pfes** | **Ptotal** |
|---|---|---|---|---|---|---|
| 4.734 mW | 6.655 mW | 1.029 mW | 0.531 mW | 0.047 mW | 0.322 mW | 8.583 mW |
| 17.290 | 11.792 | 1.609 | 2.198 | 0.618 | 0.503 | 16.719 |
| 30.495 | 18.663 | 2.149 | 4.224 | 1.819 | 0.672 | 27.527 |
| 44.200 | 24.971 | 2.686 | 6.567 | 3.522 | 0.839 | **38.585** |
| 58.344 | 33.063 | 3.236 | 9.280 | 5.671 | 1.011 | **52.261** |
| 65.536 | 37.518 | 3.510 | 10.779 | 6.839 | 1.097 | **59.743** |
| 68.925 | 40.335 | 3.726 | 11.426 | 8.873 | 1.164 | **65.525** |
| 72.107 | 43.771 | 4.027 | 12.131 | 12.365 | 1.258 | **73.553** |
| 75.002 | 47.588 | 4.385 | 12.911 | 17.020 | 1.370 | **83.274** |
| 77.767 | 51.877 | 4.806 | 13.637 | 22.801 | 1.502 | **94.623** |
| 87.835 | 72.376 | 6.927 | 16.606 | 53.026 | 2.165 | **151.100** |

*Vbat(oc) = 3.1V:*

●●● *(Fig. 5B)*

| ***Duty Cycle = 32 mW/ Ptotal*** | ***Ibat(avg)*** = DC * Ibat |
|---|---|
| 90.0 % | 1.372 mA |
| 90.0 | 4.984 |
| 90.0 | 8.744 |
| 82.9 | 11.615 |
| 61.2 | 11.256 |
| 53.6 | 11.032 |
| 48.8 | 10.562 |
| 43.5 | 9.834 |
| 38.4 | 9.024 |
| 33.8 | 8.226 |
| 21.2 | 5.795 |

| ***Duty Cycle = 25.6 mW/ Ptotal*** | ***Ibat(avg)*** = DC * Ibat |
|---|---|
| 90.0 % | 1.372 mA |
| 90.0 | 4.984 |
| 90.0 | 8.744 |
| 66.3 | 9.292 |
| 49.0 | 9.004 |
| 42.9 | 8.825 |
| 39.1 | 8.449 |
| 34.8 | 7.867 |
| 30.7 | 7.219 |
| 27.1 | 6.581 |
| 16.9 | 4.636 |

*Vbat(oc) = 3.1V:*

| ***Vnab*** | ***DC*** |
|---|---|
| 0.030 V | 90.0 % |
| 0.109 | 90.0 |
| 0.181 | 90.0 |
| ***0.243*** | ***82.9*** |
| 0.293 | 61.2 |
| 0.319 | 53.6 |
| 0.401 | 48.8 |
| 0.544 | 43.5 |
| 0.722 | 38.4 |
| 0.935 | 33.8 |
| 1.935 | 21.2 |

*Vbat(oc) = 3.3V:*

| ***Vnab*** | ***DC*** |
|---|---|
| 0.015 | 90.0 % |
| 0.057 | 90.0 |
| 0.099 | 90.0 |
| ***0.137*** | ***84.7*** |
| 0.2220 | 61.9 |

EFFICIENT EXTERNAL CHARGER FOR CHARGING A PLURALITY OF IMPLANTABLE MEDICAL DEVICES

CROSS-REFERENCE TO RELATED APPLICATIONS

This is a continuation application of U.S. patent application Ser. No. 12/624,162, filed Nov. 23, 2009 (allowed), which is incorporated by reference and to which priority is claimed.

FIELD OF THE INVENTION

The present invention relates generally to an external charger used to inductively charge a rechargeable battery within a plurality of implantable medical devices such as neurostimulators.

BACKGROUND

Implantable stimulation devices generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, occipital nerve stimulators to treat migraine headaches, and other neural stimulators to treat urinary incontinence, sleep apnea, shoulder sublaxation, etc. The present invention may find applicability in all such applications and in other implantable medical device systems, although the description that follows will generally focus on the use of the invention in a Bion™ microstimulator device system of the type disclosed in U.S. Patent Application Publication 2010/0268309.

Microstimulator devices typically comprise a small generally-cylindrical housing which carries electrodes for producing a desired stimulation current. Devices of this type are implanted proximate to the target tissue to allow the stimulation current to stimulate the target tissue to provide therapy for a wide variety of conditions and disorders. A microstimulator usually includes or carries stimulating electrodes intended to contact the patient's tissue, but may also have electrodes coupled to the body of the device via a lead or leads. A microstimulator may have two or more electrodes. Microstimulators benefit from simplicity. Because of their small size, the microstimulator can be directly implanted at a site requiring patient therapy.

FIG. 1 illustrates an exemplary implantable microstimulator 100. As shown, the microstimulator 100 includes a power source 145 such as a battery, a programmable memory 146, electrical circuitry 144, and a coil 147. These components are housed within a capsule 202, which is usually a thin, elongated cylinder, but may also be any other shape as determined by the structure of the desired target tissue, the method of implantation, the size and location of the power source 145 and/or the number and arrangement of external electrodes 142. In some embodiments, the volume of the capsule 202 is substantially equal to or less than three cubic centimeters.

The battery 145 supplies power to the various components within the microstimulator 100, such the electrical circuitry 144 and the coil 147. The battery 145 also provides power for therapeutic stimulation current sourced or sunk from the electrodes 142. The power source 145 may be a primary battery, a rechargeable battery, a capacitor, or any other suitable power source. Systems and methods for charging a rechargeable battery 145 will be described further below.

The coil 147 is configured to receive and/or emit a magnetic field that is used to communicate with, or receive power from, one or more external devices that support the implanted microstimulator 100, examples of which will be described below. Such communication and/or power transfer may be transcutaneous as is well known.

The programmable memory 146 is used at least in part for storing one or more sets of data, including electrical stimulation parameters that are safe and efficacious for a particular medical condition and/or for a particular patient. Electrical stimulation parameters control various parameters of the stimulation current applied to a target tissue including, but not limited to, the frequency, pulse width, amplitude, burst pattern (e.g., burst on time and burst off time), duty cycle or burst repeat interval, ramp on time and ramp off time of the stimulation current, etc.

The illustrated microstimulator 100 includes electrodes 142-1 and 142-2 on the exterior of the capsule 202. The electrodes 142 may be disposed at either end of the capsule 202 as illustrated, or placed along the length of the capsule. There may also be more than two electrodes arranged in an array along the length of the capsule. One of the electrodes 142 may be designated as a stimulating electrode, with the other acting as an indifferent electrode (reference node) used to complete a stimulation circuit, producing monopolar stimulation. Or, one electrode may act as a cathode while the other acts as an anode, producing bipolar stimulation. Electrodes 142 may alternatively be located at the ends of short, flexible leads. The use of such leads permits, among other things, electrical stimulation to be directed to targeted tissue (s) a short distance from the surgical fixation of the bulk of the device 100.

The electrical circuitry 144 produces the electrical stimulation pulses that are delivered to the target nerve via the electrodes 142. The electrical circuitry 144 may include one or more microprocessors or microcontrollers configured to decode stimulation parameters from memory 146 and generate the corresponding stimulation pulses. The electrical circuitry 144 will generally also include other circuitry such as the current source circuitry, the transmission and receiver circuitry coupled to coil 147, electrode output capacitors, etc.

The external surfaces of the microstimulator 100 are preferably composed of biocompatible materials. For example, the capsule 202 may be made of glass, ceramic, metal, or any other material that provides a hermetic package that excludes water but permits passage of the magnetic fields used to transmit data and/or power. The electrodes 142 may be made of a noble or refractory metal or compound, such as platinum, iridium, tantalum, titanium, titanium nitride, niobium or alloys of any of these, to avoid corrosion or electrolysis which could damage the surrounding tissues and the device.

The microstimulator 100 may also include one or more infusion outlets 201, which facilitate the infusion of one or more drugs into the target tissue. Alternatively, catheters may be coupled to the infusion outlets 201 to deliver the drug therapy to target tissue some distance from the body of the microstimulator 100. If the microstimulator 100 is configured to provide a drug stimulation using infusion outlets 201, the microstimulator 100 may also include a pump 149 that is configured to store and dispense the one or more drugs.

Turning to FIG. 2, the microstimulator 100 is illustrated as implanted in a patient 150, and further shown are various external components that may be used to support the implanted microstimulator 100. An external controller 155 may be used to program and test the microstimulator 100 via communication link 156. Such link 156 is generally a two-way link, such that the microstimulator 100 can report its status or various other parameters to the external controller 155. Communication on link 156 occurs via magnetic inductive coupling. Thus, when data is to be sent from the external controller 155 to the microstimulator 100, a coil 158 in the external controller 155 is excited to produce a magnetic field that comprises the link 156, which magnetic field is detected at the coil 147 in the microstimulator. Likewise, when data is to be sent from the microstimulator 100 to the external controller 155, the coil 147 is excited to produce a magnetic field that comprises the link 156, which magnetic field is detected at the coil 158 in the external controller. Typically, the magnetic field is modulated, for example with Frequency Shift Keying (FSK) modulation or the like, to encode the data.

An external charger 151 provides power used to recharge the battery 145 (FIG. 1). Such power transfer occurs by energizing the coil 157 in the external charger 151, which produces a magnetic field comprising link 152. This magnetic field 152 energizes the coil 147 through the patient 150's tissue, and which is rectified, filtered, and used to recharge the battery 145 as explained further below. Link 152, like link 156, can be bidirectional to allow the microstimulator 100 to report status information back to the external charger 151. For example, once the circuitry 144 in the microstimulator 100 detects that the power source 145 is fully charged, the coil 147 can signal that fact back to the external charger 151 so that charging can cease. Charging can occur at convenient intervals for the patient 150, such as every night.

FIG. 3 illustrates salient portions of the microstimulator's power circuitry 160. Charging energy (i.e., the magnetic charging field) is received at coil 147 via link 152. The coil 147 in combination with capacitor 162 comprises a resonant circuit, or tank circuit, which produces an AC voltage at Va. This AC voltage is rectified by rectifier circuitry 164, which can comprise a well-known 4-diode bridge circuit, although it is shown in FIG. 3 as a single diode for simplicity. Capacitor 166 assists to filter the signal at node Vb, such that Vb is essentially a DC voltage, although perhaps having a negligible ripple. Intervening between Vb and the rechargeable battery 145 is charging circuitry 170, which ultimately takes the DC voltage Vb and uses it to produce a controlled battery charging current, Ibat. Charging circuitry 170 is well known. One skilled in the art will recognize that the power circuitry 160 may include other components not shown for simplicity.

Depending on the patient's condition, it may be desirable to implant more than one microstimulator to provide more complex stimulation to the patient and/or to provide stimulation in different locations. For instance, as shown in the example of FIG. 4, a first microstimulator 100 is implanted at a first location, and a second microstimulator 101 is implanted at a second location. Additional microstimulators could also be implanted if more complicated therapies are indicated, but only two microstimulators are shown in FIG. 4 for simplicity. Microstimulators 100 and 101 may operate independently or may operate in a coordinated manner.

The external controller 155 can communicate with each microstimulator independently, with communications accompanied by a header containing an address of the microstimulator. Such addressing ensures no confusion when communicating with the two microstimulators 100 and 101, and thus allows each to be independently programmed and monitored by the external controller 155. Such addressing also allows the two microstimulators 100 and 101 to communicate with each other.

Both microstimulators 100 and 101 will eventually need to have their batteries recharged using external charger 151, and such charging presents special challenges. Each of the microstimulators 100 and 101 could be charged independently, but this would take additional time. Even if a patient had only two microstimulators implanted, the total time to charge both would roughly double compared to a single implant, which would comprise a major inconvenience to the patient. Independent charging of the microstimulators also requires some coordination between the microstimulators 100 and 101. For example, the microcontrollers 100 and 101 would have to know when to enable or disable charging by opening or connecting their coils 147.

Because of such issues, the inventors consider it preferable to charge both microstimulators 100 and 101 at the same time. However, while this approach would provide for faster charging, it is a challenge to optimize and to do so safely. Of particular concern is implant heating, which one skilled in the art will understand is an inevitable side effect of charging using magnetic fields. Heating can result from several different sources, such as eddy currents in conductive portions of the implant, or heating of the various components in the power circuitry 160. Implant heating is a serious safety concern; if an implant exceeds a given safe temperature (e.g., 41° C.), the tissue surrounding the implant may be aggravated or damaged.

Generally speaking, implant heating is a function of both the strength of the magnetic charging field, and the coupling between the external charger 151 and the implant. The strength of the magnetic charging field can be increased by increasing the excitation current in the coil 157 of the external charger 151. Increasing the magnetic charging field will increase the current/voltage induced in the coil 147 of the microstimulator 100, which increases the battery charging current, Ibat (FIG. 3). Increasing the battery charging current speeds up charging, but also increases heat dissipation in the device.

Coupling between the external charger 151 and the implant affects how readily the magnetic charging field is passed to the implant, i.e., how strongly the effect of the magnetic charging field is felt at the implant. Many factors affecting coupling, such as the inductances of the coil 157 in the external charger 151 and the coil 147 in the implant, alignment, angle and distance between the coils 151 and 147, the permittivity of any materials (e.g., tissue, air) between the coils, etc. Coupling between an external charger and an implant is discussed further in U.S. Pat. No. 8,473,066. Generally speaking, if the coupling between the coils is relatively high, a relatively large current/voltage will be induced in implant coil 147, leading to faster charging and higher power dissipation (higher temperatures) in the implant.

Because of differences in the placement of multiple microstimulators in a patient, one could expect that the coupling between the external charger 151 and those microstimulators would differ. This means that the same magnetic charging field produced by the external charger 151 would result in different amounts of power in each of the microstimulators. Consider FIG. 4: microstimulator 101 is located deeper in the patient, and is therefore farther away from the external charger 151 than is microstimulator 100. Moreover, the angle θ between the coil 147 in microstimulator 101 and coil 157 in external charger 151 is relatively large, and the offset of their axes D is relatively large. These factors all contribute to low coupling between the external charger 157 and microstimulator 101 as compared to microstimulator 100.

As a result, when the external charger 151 produces a magnetic charging field, microstimulator 100 will charge more quickly—and will generate more heat—than will microstimulator 101. As noted, this makes optimization difficult. If the generated magnetic charging field is optimized to charge microstimulator 101 as quickly as possible at a safe temperature, then microstimulator 100 would become too hot. By contrast, if the generated magnetic charging field is optimized to charge microstimulator 100 as quickly as possible at a safe temperature, then microstimulator 101 would charge too slowly.

Finding optimal charging conditions (intensity, duty cycle) when simultaneously charging multiple implants is the subject of this disclosure, and solutions to this problems are disclosed herein.

DETAILED DESCRIPTION

An improved external charger for a battery in an implantable medical device (implant), and techniques for simultaneously charging batteries in multiple implants using such improved external charger, is disclosed. In one example, simulation data is used to model the power dissipation of the charging circuitry in an implant at varying levels of implant power. A power dissipation limit is chosen to constrain the charging circuitry from producing an inordinate amount of heat to the tissue surrounding the implant, and duty cycles are determined for the various levels of input intensities to ensure that the power limit is not exceeded. A maximum simulated average battery current determines the optimal (i.e., quickest) battery charging current, and at least an optimal value for a parameter indicative of that current, for example, the voltage across the battery charging circuitry, is determined and stored in the external charger.

During charging, the actual value for that parameter is reported from multiple implants to the external charger. The external charger infers from the magnitudes of the parameters which of the implants has the highest and lowest coupling to the external charger, and so designates those implants as "hot" and "cold." The intensity of the magnetic charging field is optimized for the cold implant consistent with the simulation to ensure that the cold implant is charged with a maximum (fastest) battery charging current. The duty cycle of the magnetic charging field is also optimized for the hot implant consistent with the simulation to ensure that the hot implant does not exceed the power dissipation limit. As a result, charging is optimized to be fast for all of the implants, while still safe from a tissue heating perspective.

Prior to discussing the optimization of charging batteries in multiple implants, a technique for optimizing the charging of a battery in a single implant is discussed with reference to FIGS. 5A-12, which subject matter is disclosed in U.S. Patent Application Publication 2001/0087307, which is incorporated herein by reference.

Figure 1:
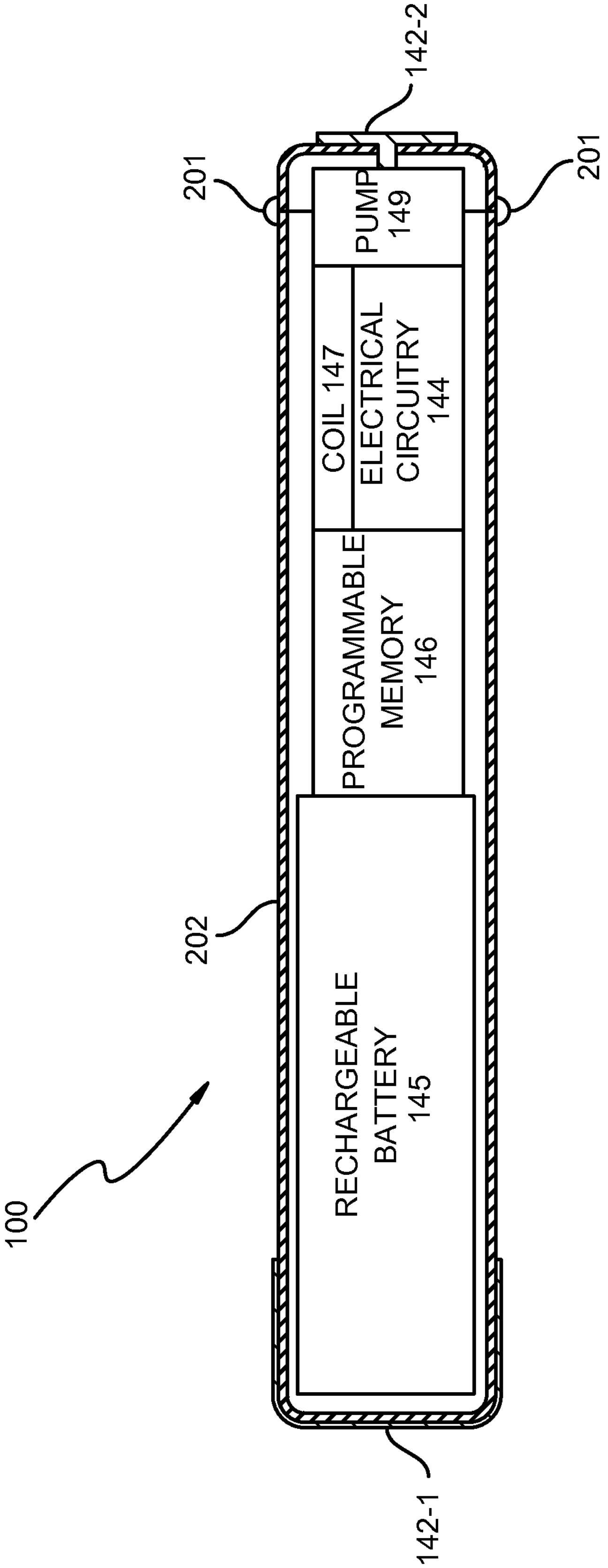
FIG. 1 illustrates a microstimulator implant, including a battery requiring periodical recharging from an external charger, in accordance with the prior art.
Figure 2:
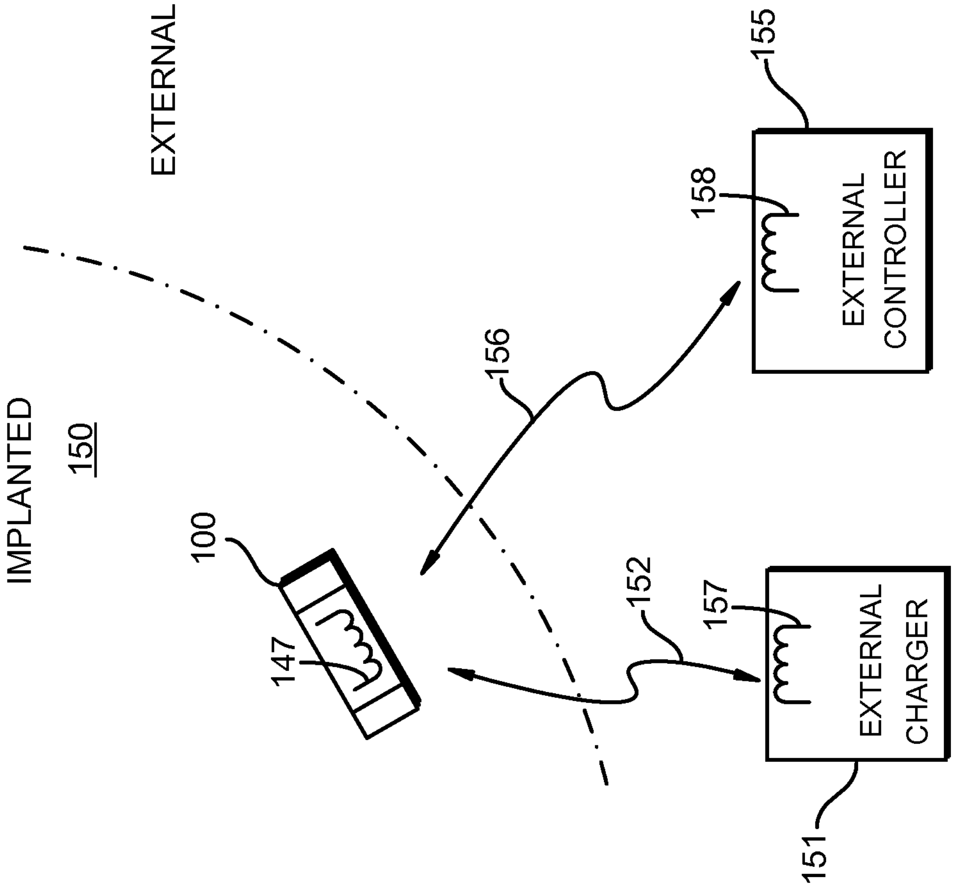
FIG. 2 shows the implant in communication with, inter alia, an external charger in accordance with the prior art.
Figure 3:
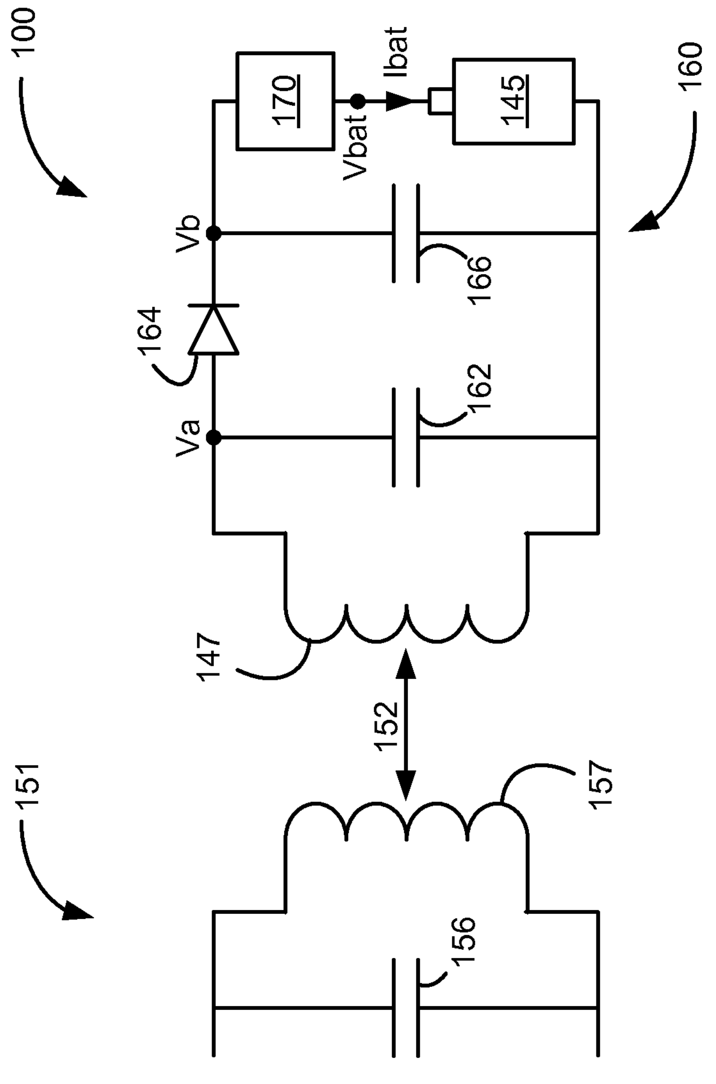
FIG. 3 illustrates charging circuitry within the implant in accordance with the prior art.

Reference is made to the microstimulator power circuitry 160 of FIG. 3. While this circuitry is exemplary, it should be understood that the disclosed technique is not limited to use with the particular power circuitry 160 shown.

Various components in the power circuitry 160 within the implant will draw power during the reception of a magnetic charging field from the external charger 151. In particular, the coil 147, its associated tank capacitor 162, the rectification circuitry (diode) 164, charging circuitry 170, and the battery 145 itself will all dissipate power in the form of heat. (Capacitor 166 will draw a comparatively negligible amount of power, and thus is not further discussed). The sum total of the powers dissipated by each of these components must be considered when understanding how the tissue surrounding the implant 100 will heat up during a charging session. For example, animal studies show that for a particular multiple-electrode microstimulator device, a radiated power of 32 mW will raise the temperature of the tissue surrounding the implant by approximately 4° C., while a total radiated power of 25.6 mW will raise the temperature by 3.2° C. Of course, these values are only exemplary, and could vary; future values could be determined that are more accurate, safer, etc. In any event, such animal studies have correlated power dissipation to tissue heating for a given implant.

It is desired to keep the total dissipated power at or below a limit to ensure that the patient's tissue will not overheat. Because a 4° C. rise in tissue temperature is generally accepted as safe for a patient, one example of the technique labors to keep the total power dissipated from the power circuitry 160 at or below 32 mW. Of course, different limits could be chosen, such as the 25.6 mW/3.2° C. limit discussed above.

Figure 5A:
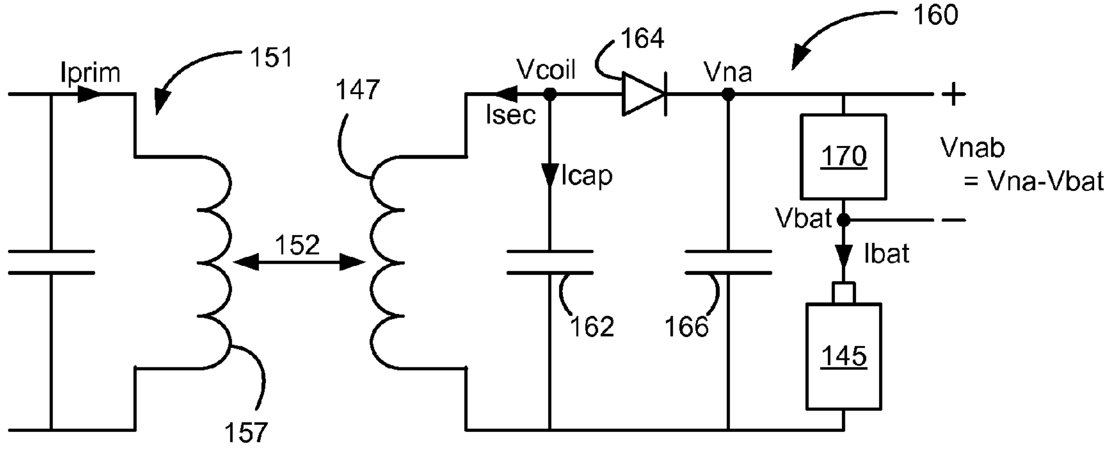
FIGS. 5A-5C illustrate a simulation in accordance with one example.
Figure 5B:
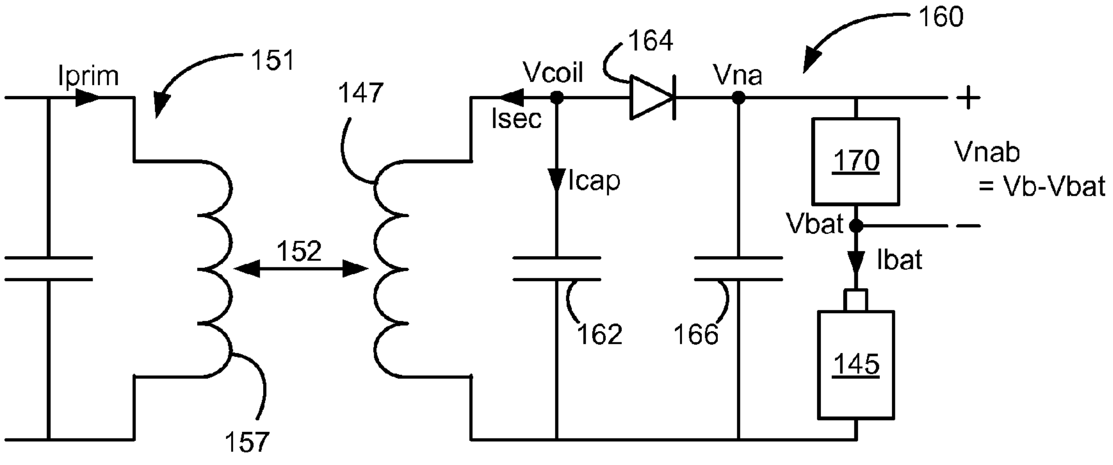
Figure 5C:
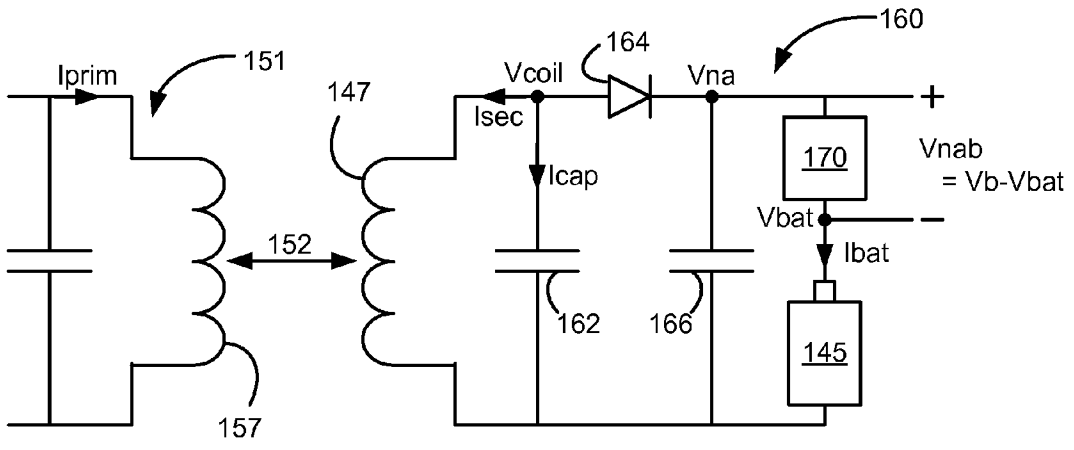

Simulations show that power dissipation from the various components in the power circuitry 160 is complex and non-linear in nature. One such simulation 200 is illustrated in FIGS. 5A, 5B, and 5C. As will be discussed further below, certain portions from simulation 200 are preferably stored in the external charger 151 and will be used to regulate charging. However, before discussing a charging operation, simulation 200 is explained.

Simulation 200 shows the effect of varying the intensity (e.g., current) in the external controller's charging coil 157 (Iprim(rms)) on the various components in the power circuitry 160 of the implant 100, with each successive row representing an increasing value for Iprim(rms). Because the simulation 200 results will vary depending on how full or depleted the implant battery 145 is at a given moment, the depicted simulation assumes a battery with a particular open-circuit voltage of Vbat(oc)=3.1 V. Although not depicted, other simulations 200 at other open circuit battery voltages (e.g., 3.3V, 3.7V, 4.1V, etc.) may also be generated to provide accurate simulation results as battery capacity starts to fill during charging. For example, if the battery 145 has a full capacity of Vbat(oc)=4.1V, then simulations 200 may be generated for Vbat(oc)=3.1 V, 3.3V, 3.7V, and 4.1V to cover a range of expected battery capacity. However, if the various parameters within simulation 200 do not vary appreciably with Vbat(oc), then the generation of additional simulations 200 for different battery capacities may not be necessary. A simulation program useful in generating a simulation 200 is Mentor Graphics Design Architect.

The simulation 200 assumes a particular coupling factor between the primary coil 157 in the external charger 151 and the secondary coil 147 in the implant 100, which coupling factor is modeled taking into account factors affecting such coupling, such as coil inductances, coil alignment, the distance and permittivity of any materials (e.g., tissue, air) between the coils, etc. In the depicted simulation, a coupling factor k=0.017 was chosen to conservatively simulate a worst case alignment between the charging coils 157 and 147. In any event, the coupling factor ultimately results in a simulated induced current in charging coil 147 in the implant (Isec (rms)), a current in the associated tank capacitor 162 (Icap (rms)), a voltage across the coil 147 (Vcoil(rms)), a DC voltage produced by the rectifier circuit (diode) 164 (Vna), a battery charging current (Ibat), and a battery voltage (Vbat) resulting from the input of the battery charging current, which battery voltage takes into account the internal resistance of the battery 145 and which is therefore different from the open-circuit battery voltage, Vbat(oc). Of course, relevant parameters for the various components in the power circuitry 160 (resistances, capacitance, inductances, coupling factor, etc.) are input into the simulation program to allow it to generate the simulation results.

Figure 6:
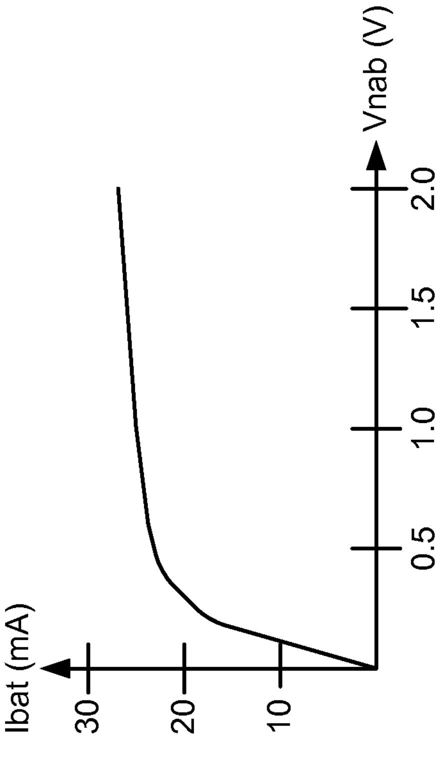
FIG. 6 illustrates the relation between battery charging current (Ibat) and the voltage across the battery protection circuitry (Vnab) as revealed from the simulation of FIG. 5.

Of particular interest in simulation 200 is the voltage across the charging circuitry 170, Vnab, which represents the difference between Vna and Vbat. Because the charging circuitry 170 is in line with the battery charging current, Ibat, any excessive voltage build up across the charging circuitry comprises undesired heat generation. Unfortunately, modeling shows that the amount of heat dissipation from the charging circuitry 170 increases essentially exponentially as the battery charging current increases. This is shown in FIG. 6: as the battery charging current Ibat increases, the voltage built up across the battery protection circuitry Vnab increases at an increasingly fast rate. Because the power dissipated by the charging circuit 170 equals the current times the voltage, the power too essentially exponentially increases. In short, the parameter Vnab correlates with excessive charging power wasted as heat, and as will be seen below, is monitored and controlled in the disclosed technique to permit charging at an optimally efficient level.

From the various simulated voltages and currents in FIG. 5A, the simulation 200 can further calculate the power dissipated by the various components in the power circuitry 160, as shown in FIG. 5B, which powers essentially comprise the product of the voltage across and current through the various components. As shown, the power drawn by each component is represented by the element numeral for the component: for example, the power drawn by the battery 145 during charging is denoted as P145. Pfes represents power drawn by front end switches in series with the charging circuitry 170, which switches are not depicted for simplicity because their power dissipations are relatively small. The sum of the power dissipated by each of the components in the power circuitry 160 is shown in the last column in FIG. 5B (Ptotal).

A review of the Ptotal parameter in simulation 200 illustrates a tissue heating concern for the designer. As discussed earlier, an acceptable level of total power dissipated by the power circuitry 160 should not exceed the 32 mW power dissipation limit in one example—a temperature known by experimentation to increase surrounding tissue by 4° C. However, all but the top three rows in FIG. 5B exceed this value (bolded for easy viewing). In other words, simulation 200 shows that at higher external charger intensities (i.e., higher Iprim(rms)), the total heat generated in the implant 100 may be excessive.

One solution to keep the total power at or below 32 mW is to duty cycle the power at the external charger 151, which computed duty cycle is shown in FIG. 5C. The duty cycle ensures that the power dissipation limit is not exceeded by dividing the limit (e.g., 32 mW) by the simulated total power draw assuming no duty cycling (Ptotal).

Figure 7:
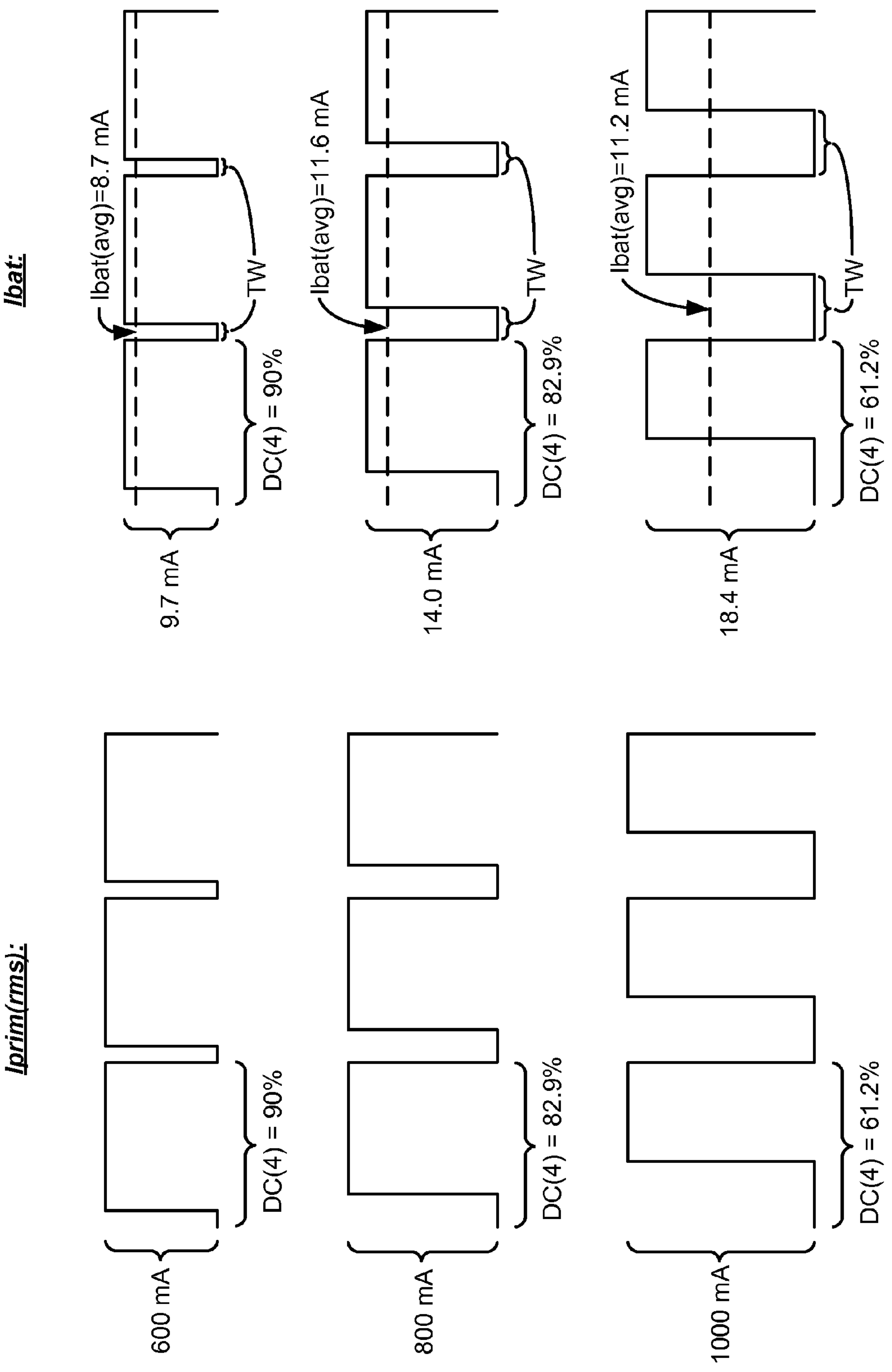
FIG. 7 illustrates various duty cycles determined for the simulation of FIG. 5 which will not exceed a prescribed power limit, and shows the application of such duty cycles on the power at the external charging coil (Iprim(rms)) and in the battery charging current (Ibat).

The results of such duty cycling are shown in FIG. 7 for the third, fourth, and fifth rows in the simulation 200, i.e., when Iprim(rms) equals 600, 800, and 1000 mA. In the third row, the simulated total power dissipated was 27.5 mW, which is below the 32 mW limit. Hence, duty cycling would not be required for this level of input power (i.e., for Iprim(rms)=600 mA). However, a duty cycle of 90% is imposed anyway to allow an off time, or telemetry window (TW), during which the implant 100 can back-telemeter data to the external charger 151. The telemetry window (TW) may be 10 sec for example, meaning that the period for duty cycling is typically about 10 times larger, or 100 sec. While the telemetry window TW can be fixed, it can also be made to vary depending on how long is needed to send data back to the external charger 151. For example, the TW can be set to the exact time needed for data transmission, with the on portion of the cycle similarly scaled to match the duty cycle required. A shorter duration for the total period of the duty cycle reduces ripple in the temperature of the implant 100.

As will be seen further below, it is advantageous to telemeter data (e.g., Vnab, Vbat(oc)) back to the external charger 151 during off periods of the duty cycle to allow charging to be iteratively optimized in real time. As can be seen in FIG. 7, this duty cycle is imposed on the primary coil in the external charger (Iprim(rms)), which causes the same duty cycle in the battery charging current, Ibat. An average battery current, Ibat(avg), can be calculated from the product of Ibat and the duty cycle to give an over-time indication of the amount of charging current that is being received by the battery, despite the duty cycling. The significance of Ibat(avg) will be discussed further below.

In the fourth row of the simulation 200 (Iprim(rms)=800 mA), the simulated total power dissipated was 38.6 mW, above the 32 mW limit. Therefore, duty cycling is imposed as a heat control measure, in addition to the desire for an off period to allow for back telemetry. Such duty cycling equals 82.9% (32/38.6) to ensure a total dissipated power of not more than 32 mW. The fifth row is similarly processed to determine a duty cycle of 61.2%, and its effects on Iprim(rms) and Ibat are shown.

Additionally shown to the right in FIG. 5C are the computed duty cycles for the less-heat-intensive 25.6 mW/3.2° C. limit, which limit may be chosen to even further minimize patient discomfort or injury due to heat generation in the power circuitry 160. Again, the duty cycles are computed by dividing the limit (25.6 mW) by the simulated total powers (Ptotal).

Note from FIG. 7 that the average battery current, Ibat (avg), is maximized when Iprim equals 800 mA. This average maximum, Ibat(avg)(opt)=11.6 mA, represents the optimal charging current for the implant battery 145: it is the largest average current and hence will charge the implant battery the fastest. Moreover, because of the duty cycling leading to the calculation of the Ibat(avg) values, Ibat(avg)(opt) is at the same time optimized to allow no more than 32 mW power dissipation on average. Ibat(avg)(opt) is thus optimized for both speed and heat dissipation.

Figure 8:
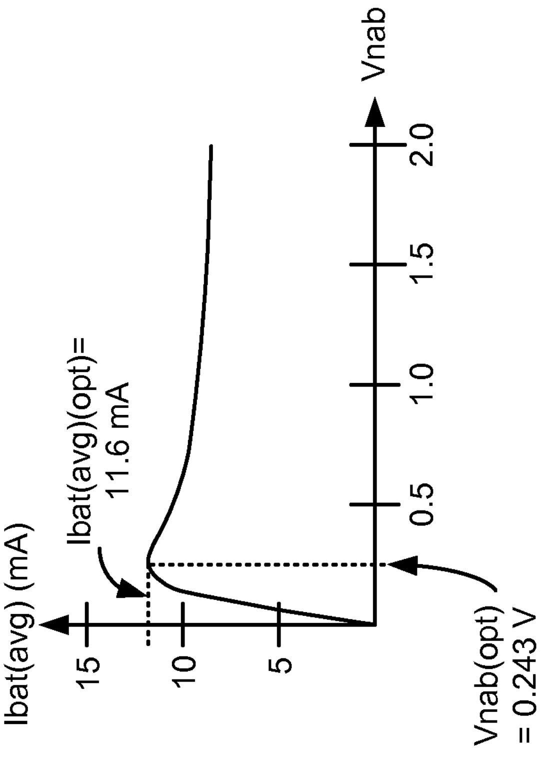
FIG. 8 illustrates the relation between the average battery charging current (Ibat(avg)) and Vnab as revealed from the simulation of FIG. 5, and shows the Vnab(opt) at which Ibat(avg) is maximized.

To maintain Ibat(avg)(opt) during charging, it is useful to monitor a parameter indicative of the battery charging current, Ibat. One convenient parameter comprises Vnab, i.e., the voltage that builds across the charging circuitry 170, although other parameters indicative of the battery charging current could also be used (e.g., Vna). The Vnab parameter is easily measured in the implant, and as noted earlier represents wasted heat. FIG. 8 shows a graph of Ibat(avg) v. Vnab for the simulation 200 for the 32 mW/4° C. limit, and shows the maximum at 11.6 mA. The corresponding Vnab for this value, Vnab(opt) is 0.243 V (see fourth row, FIG. 5A). Vnab(opt) thus represents the voltage across the charging circuitry 170 that provides the quickest charging of the implant battery 145, but which is safe from a heating perspective. As will be seen below, it is preferable to maintain Vnab at Vnab(opt) during charging.

Figure 9:
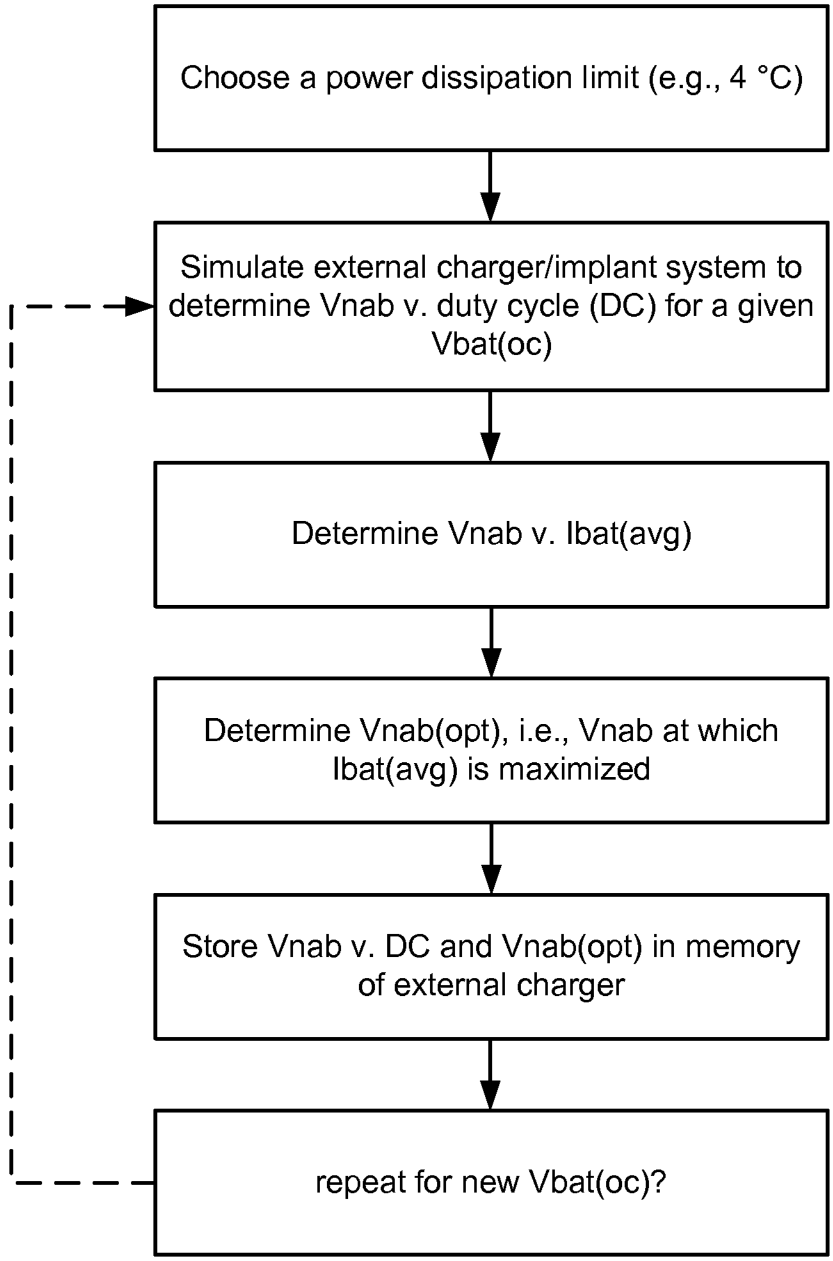
FIG. 9 illustrates storage of salient portions of the simulation to prepare the external charger for operation during an actual charging session, in accordance with one embodiment.

Prior to discussing an actual charging session, steps to this point in the process are summarized in FIG. 9, which steps lead to storing relevant parameters in the external charger 151. First, a power dissipation limit is chosen, such as the 32 mW/4° C. limit discussed previously. Then, the external charger 151/implant 100 system is simulated to determine the relationship between Vnab and the duty cycle needed to stay compliant with the power dissipation limit. This simulation can occur assuming a particular open-circuit battery voltage (Vbat(oc)) for the battery 145 in the implant 100. Next, the relationship between Vnab and Ibat(avg) is determined using the duty cycle, and an optimal Vnab(opt) is determined which corresponds to the maximum Ibat(avg). Thereafter, Vnab v. DC, and Vnab(opt) are stored in memory of the external charger (or the implant so that it could be made accessible to the external charger), as will be discussed further shortly. Thereafter, the preparation process repeats for a new battery voltage Vbat(oc) if necessary, but as noted earlier this may not be required if the various simulated parameters do not vary strongly with Vbat(oc).

Figure 10:
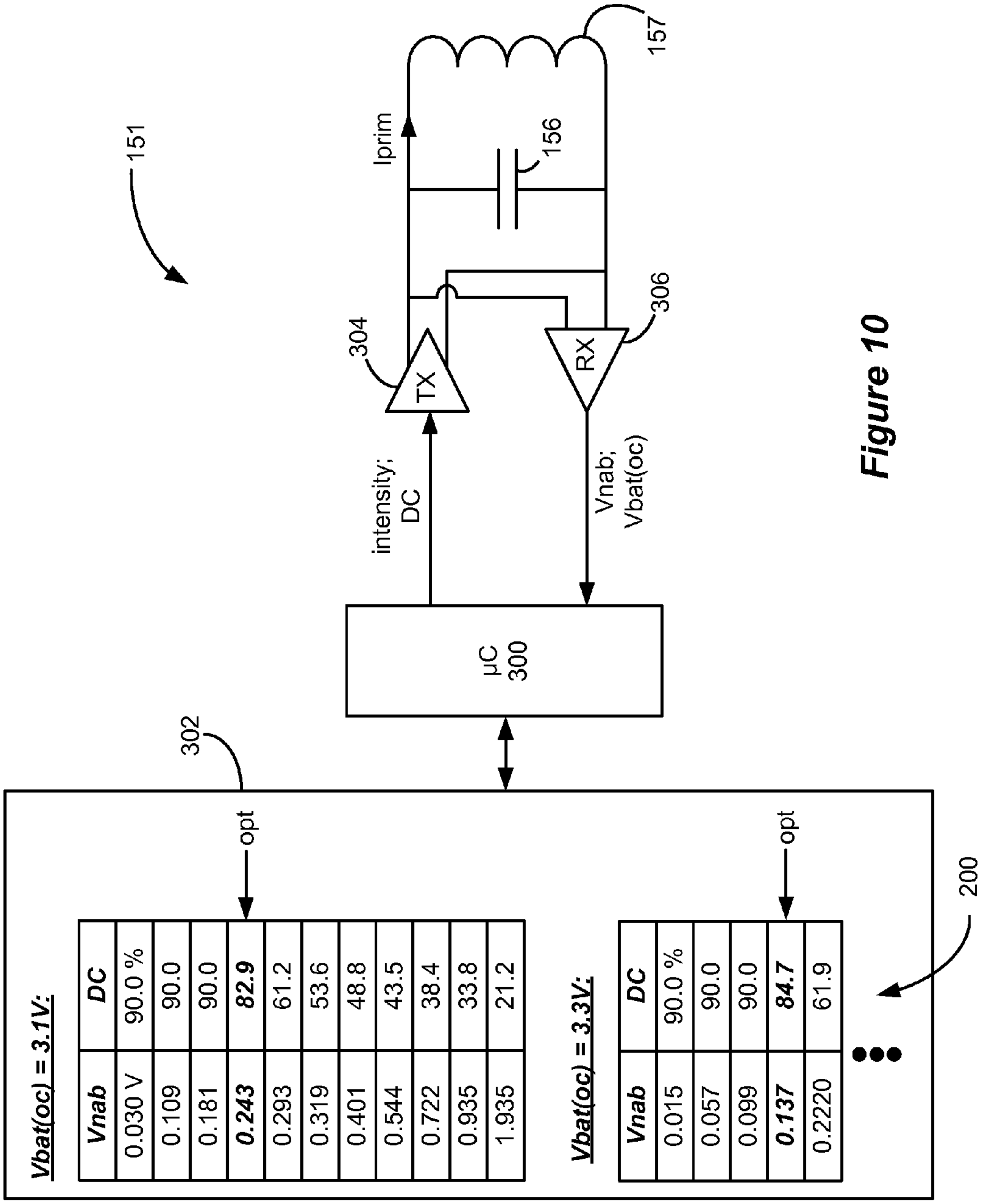
FIG. 10 illustrates circuitry in the external charger in accordance with one embodiment, including a memory storing salient portions of the simulation relevant to optimization of the charger's power parameters.

FIG. 10 shows the external charger 151 as prepared with the parameters stored from FIG. 9. Shown with particularity is a memory 302, which contains at least a portion of the simulation 200, including the Vnab v. DC relationship for the 32 mW power dissipation limit and Vnab(opt) for Vbat(oc) =3.1V. Also shown in part is the same information for Vbat (oc)=3.3V, although as just discussed this is not strictly necessary. Alternatively, memory 302 could contain the same information for other power dissipation limits (e.g., 25.6 mW/3.2° C.) as well, but this is not shown for simplicity. The memory 302 containing these parameters is coupled to (or could comprise part of) the microcontroller 300 in the external charger 151.

Also shown in FIG. 10 are the transmitter 304 and receiver 306 circuits coupled to the external charger's coil 157, which circuitry is well known. The transmitter 304 produces an AC signal to cause the L-C tank circuit (156/157) to resonate and in turn generate the magnetic charging field. As shown, the transmitter 304 receives control signals from the microcontroller 300 to indicate the intensity (e.g., the magnitude of Iprim) and the duty cycle of the transmitter 304. The receiver 306 receives data transmitted periodically from the implant 100, e.g., during the telemetry window (TW) or off portions of the duty cycle (see FIG. 7). Such data may be transmitted using radio-frequency (RF) telemetry, or Load Shift Keying (LSK) for example. (LSK is further discussed in U.S. Patent Application Publication 2010/0179618 for example).

Traditionally, such back telemetry from the implant to the external charger is used to transmit the capacity (fullness level) of the battery 145 during charging (Vbat(oc)), which informs the external charger 151 when the battery is full and that charging can cease. Battery capacity is similarly reported in the disclosed system, but additionally, the Vnab value measured at the implant 100 is also transmitted. Reporting of Vnab to the external charger 151 can take place at any suitable interval during charging, such as once every 100 seconds or so. The more frequently Vnab is reported, the more frequently charging can be optimized during the charging session.

Figure 11:
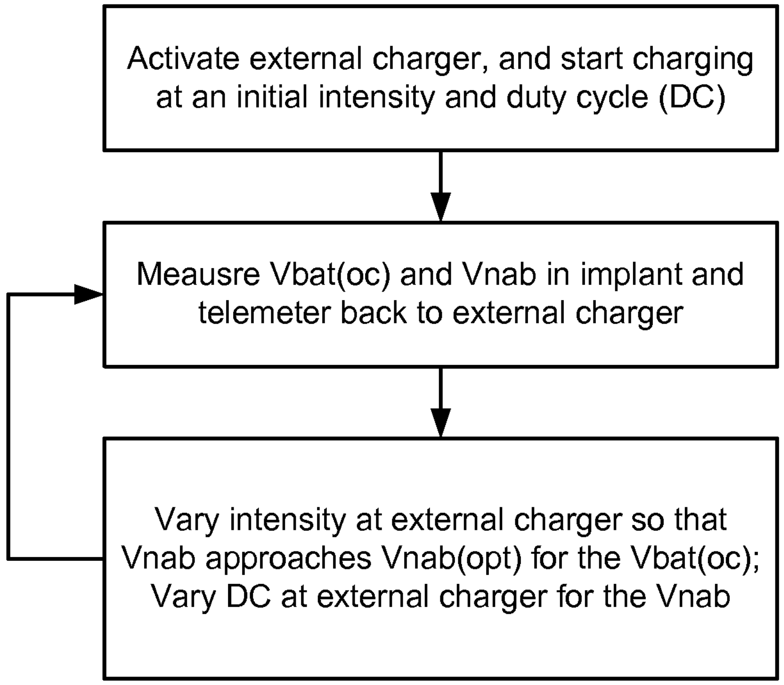
FIG. 11 illustrates a process for adjusting the power level and/or duty cycle of the power at the external charger in accordance with the stored simulation parameters.

With the basic structure of the external charger 151 understood, attention can now focus on how charger 151 operates during an actual charging session, which basic steps are shown in FIG. 11. First, the external charger 151 is turned on (e.g., by the patient), and generates a magnetic charging field using an initial intensity level (i.e., an initial Iprim) and an initial duty cycle. Simulation 200 does not help much in determining initial values for the power and duty cycle levels used at the external charger, as the coupling to the implant 100 during a real charging session cannot be perfectly known in advance. For example, different patients may have their implants located at different depths in their tissues, or may have different physical alignments between their external chargers and their implants. In any event, the initial power and duty cycle values are not important as they will be changed in accordance with the disclosed technique as charging progresses, although they are logically set to initial values guaranteed not to injure the patient. For example, in one implementation, an alignment period is instigated when charging is initiated with the intent of quickly adjust the primary current to reach the target value. During this alignment period, relatively short duration on times of the charging field are used (enough to provide an adequate read of Vbat (oc), Vnab, etc.) to adjust the primary current. Once the target primary current is reached, the external charger will apply the target duty cycle identified as optimal.

After the alignment period in which gross initial power and duty cycle values are achieved, periodically, for example, perhaps every 100 seconds, the battery voltage (Vbat(oc)) and the voltage across the charging circuitry (Vnab) are measured at the implant 100, and telemetered to the external charger. Again, such telemetry can comprise RF or LSK telemetry performed during the telemetry window (TW) or off periods in the duty cycle. How often to communicate, just like the time used for communication during the telemetry window (TW), may also be determined by the length of the needed communication between implant and charger. Increasing the frequency of communication will reduce temperature ripple in the implant 100.

Once Vnab is reported, the microcontroller 300 consults memory 302 to see if Vnab is optimal, i.e., if Vnab=Vnab(opt) for the reported Vbat(oc). If not, intensity of the magnetic charging field is changed. For example, and referring to memory 302 in FIG. 10, if Vnab is near 0.293V for Vbat(oc) =3.1V, the microcontroller 300 would understand that the intensity is too high, and would reduce Iprim in an attempt to make Vnab approach Vnab(opt). Conversely, if Vnab is near 0.181V, Iprim would be increased.

At the same time, the duty cycle of the magnetic charging field would also be changed to match the Vnab being reported. Modifying the duty cycle to match Vnab is important to ensure proper compliance with the power dissipation limit. For example, and referring again to FIG. 10, assume again that Vnab is near 0.293V, but that the duty cycle currently imposed at the transmitter 304 is 85%. Reference to the stored parameters in memory 302 shows that this duty cycle is too high, and will produce too much heat, i.e., more than the 32 mW power dissipation limit. To keep the total dissipated power compliant with the limit, the microcontroller 300, upon consulting memory 302, will change the duty cycle to 61.2%.

As shown in FIG. 11, once such intensity and duty cycle adjustments are made at the external charger 151, the process repeats: Vbat(oc) and Vnab are again reported after some time, and the intensity and duty cycle adjusted again if necessary. It should be noted that such iterative adjustment of the power produced by the external charger 151 is particularly helpful in applications where the coupling between the external charger 151 and the implant 100 might change. For example, the patient may move the external charger relative to the implant during the charging sessions. Such coupling changes can be compensated for using the disclosed technique, with adjustments made in situ to ensure the fastest charging within safe temperature limits.

Figure 12:
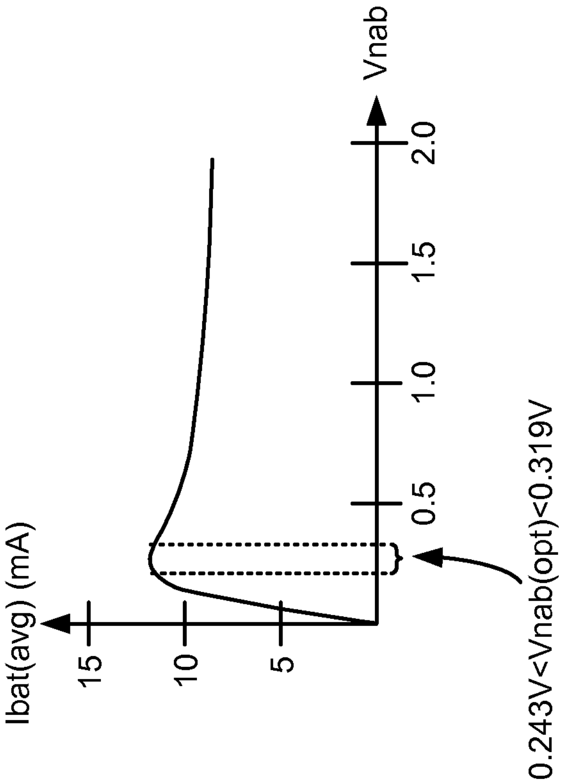
FIG. 12 illustrates application of the technique assuming definition of an optimal range for Vnab(opt).

To this point in the disclosure, it has been assumed that there is a single optimal Vnab value, Vnab(opt). However, Vnab(opt) can also represent a range of acceptable Vnab values. For example, the simulation 200 in FIG. 5C shows three values for Ibat(avg) over 11 mA (rows four through six), which correspond to Vnab values (FIG. 5A) of 0.243 to 0.319V. Assuming that operation at any of these battery charging currents provides satisfactorily quick charging of the implant battery 145, Vnab(opt) can be set to a range between 0.243 to 0.319V, as illustrated in FIG. 12. Therefore, if Vnab is reported within this range, the intensity at the external charger (Iprim) would not be changed. However, even if the intensity is not changed, it may still be prudent to vary the duty cycle in accordance with Vnab to ensure compliance with the heat limit. In this regard, notice in FIG. 5C that although Ibat(avg) does not change appreciably across the specified Vnab range (from 11.6 to 11.0 mA), the duty cycle changes rather sharply (from 82.9 to 53.6%). However, depending on the particulars of the simulation, and the conservative nature of the heat limit chosen, changing duty cycling within the Vnab(opt) range might not be necessary. In any event, defining Vnab(opt) as a range will simplify operation of the technique, and will require less frequent modification of the magnetic charging field at the external charger 151.

Now that a technique for optimization of the charging of a single implant has been discussed, attention can be turned to application of that technique to the optimization of the charging of multiple implants.

As noted earlier, when the external charger 151 produces a magnetic charging field to simultaneously charge multiple implants, the implants will charge at different rates depending on their coupling with respect to the external charger. Those implants with a high coupling factor may charge too fast (too hot), while those with a low coupling will charge too slowly. In short, it has been difficult to optimize the charging procedure to ensure quick charging without the risk of overheating.

Figure 13:
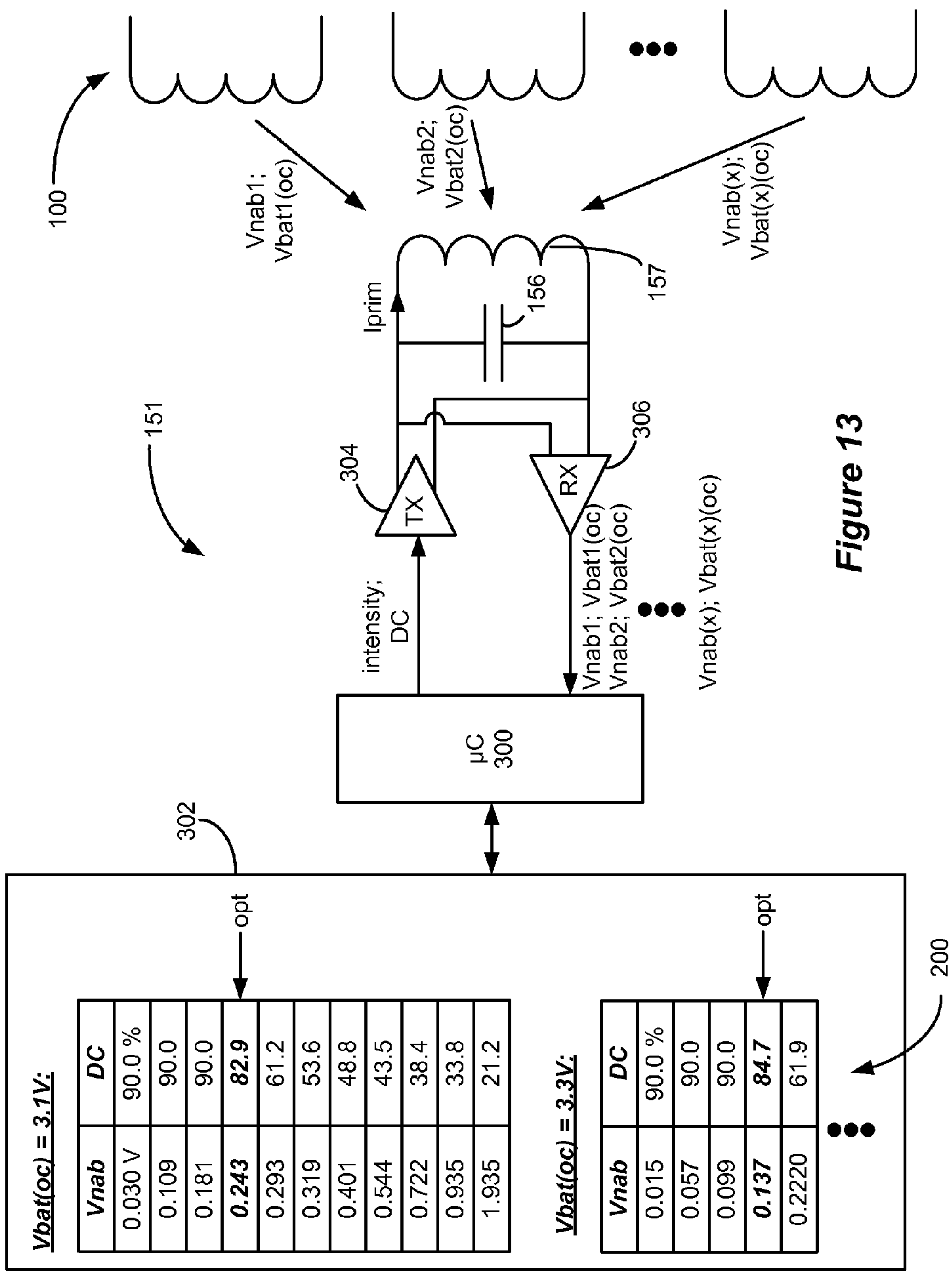
FIG. 13 illustrates a system including an external charger and a plurality of implants for simultaneously charging those implants efficiently and without exceeding a power dissipation limit for the implants.

FIG. 13 shows a system for such charging optimization, including an improved external charger 151 for charging ‘x’ implants 100. Similar to FIG. 10, the external charger 151 is prepared with the parameters stored from FIG. 9. Once again, a memory 302 contains the Vnab v. DC relationship for the 32 mW power dissipation limit and Vnab(opt) for Vbat(oc) =3.1V. Again, this same information for other values of Vbat (oc) could also be stored, as could the values for other power dissipation limits (e.g., 25.6 mW/3.2° C.).

As shown, each of the ‘x’ implants reports their measured Vnab and Vbat(oc) values back to the external charger 151 during charging. Although not shown, it should be understood that any given implant’s transmission of these parameters would likely be accompanied by an address, which address would differ for each implant. Such address allows the external charger 151 to know which Vnab and Vbat(oc) came from which of the ‘x’ implants 100, i.e., Vnab1 and Vbat1(oc) from implant1, etc.

Figure 14:
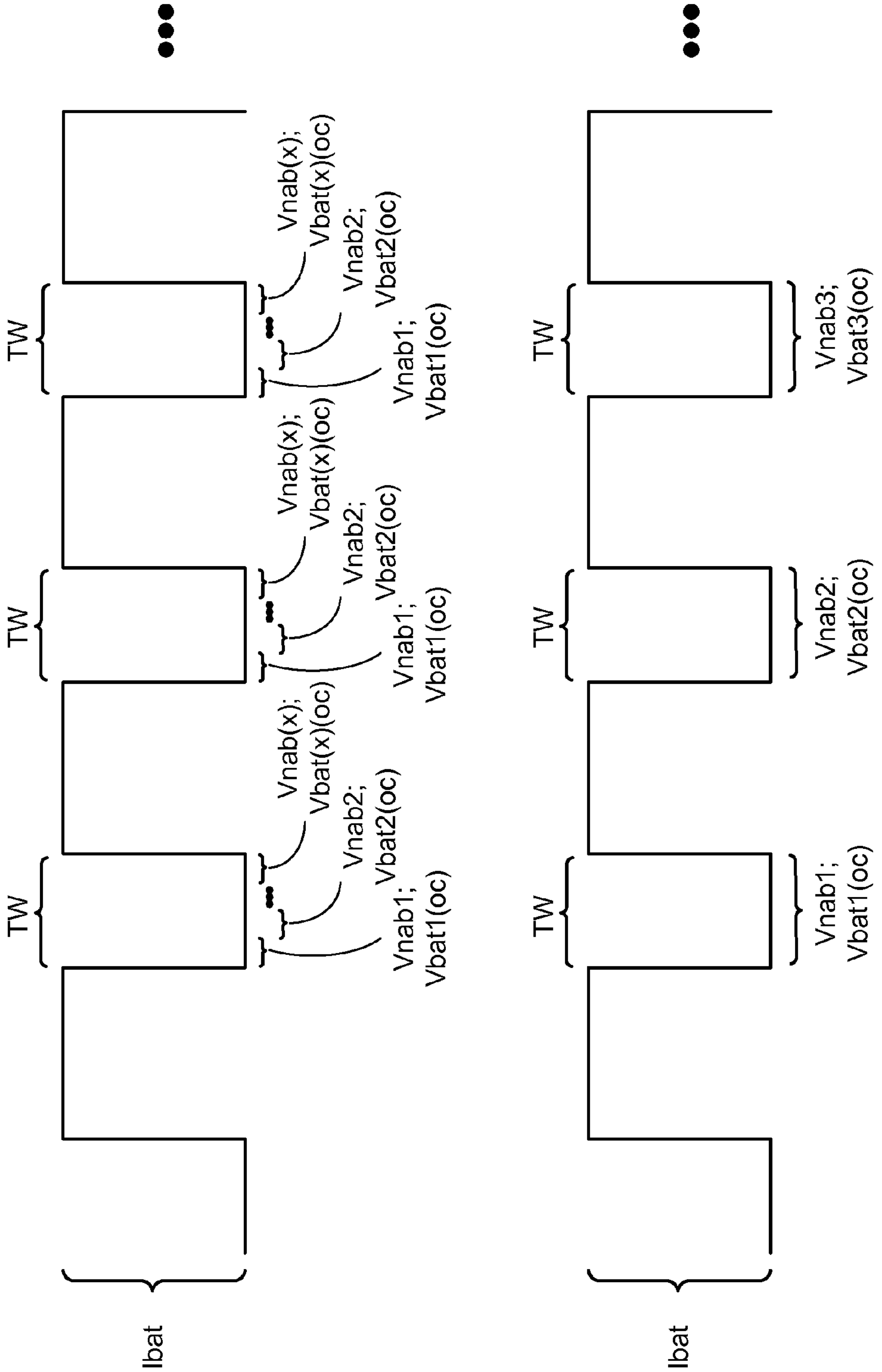
FIG. 14 illustrates examples of how Vnab can be transmitted from each implant to the external charger in an organized fashion.

As before, transmission of these parameters from the implants to the external charger 151 would preferably occur during off periods of the charger’s duty cycle. Because more than one implant 100 is involved, it is beneficial to organize the transmission from each implant to ensure that the transmissions do not overlap. Two examples of how the transmissions can be ordered are shown in FIG. 14. As shown at the top, each of the implants can be allotted a portion of the off period. Or, as shown at the bottom, the implants can take turns occupying the entirety of successive off periods. As before, depending on the length of the transmission(s) during the off period, the length of the on portion can be scaled accordingly to keep the duty cycle of the magnetic charging field at a prescribed value. Controlling the various implants to transmit in either of these fashions can be facilitated by communications between the implants. For example, implant1 can signal to implant2 when it is finished transmitting its data (Vnab1, Vbat1 (oc)), so that implant2 can begin its transfer, etc. Such inter-implant communications are facilitated when the magnetic charging field is not present during the off periods. Alternatively, the implants may be programmed to transmit only during pre-defined non-overlapping time slots. It is not important to application of the invention how the relevant parameters are transmitted to the external charger 151.

Figure 15:
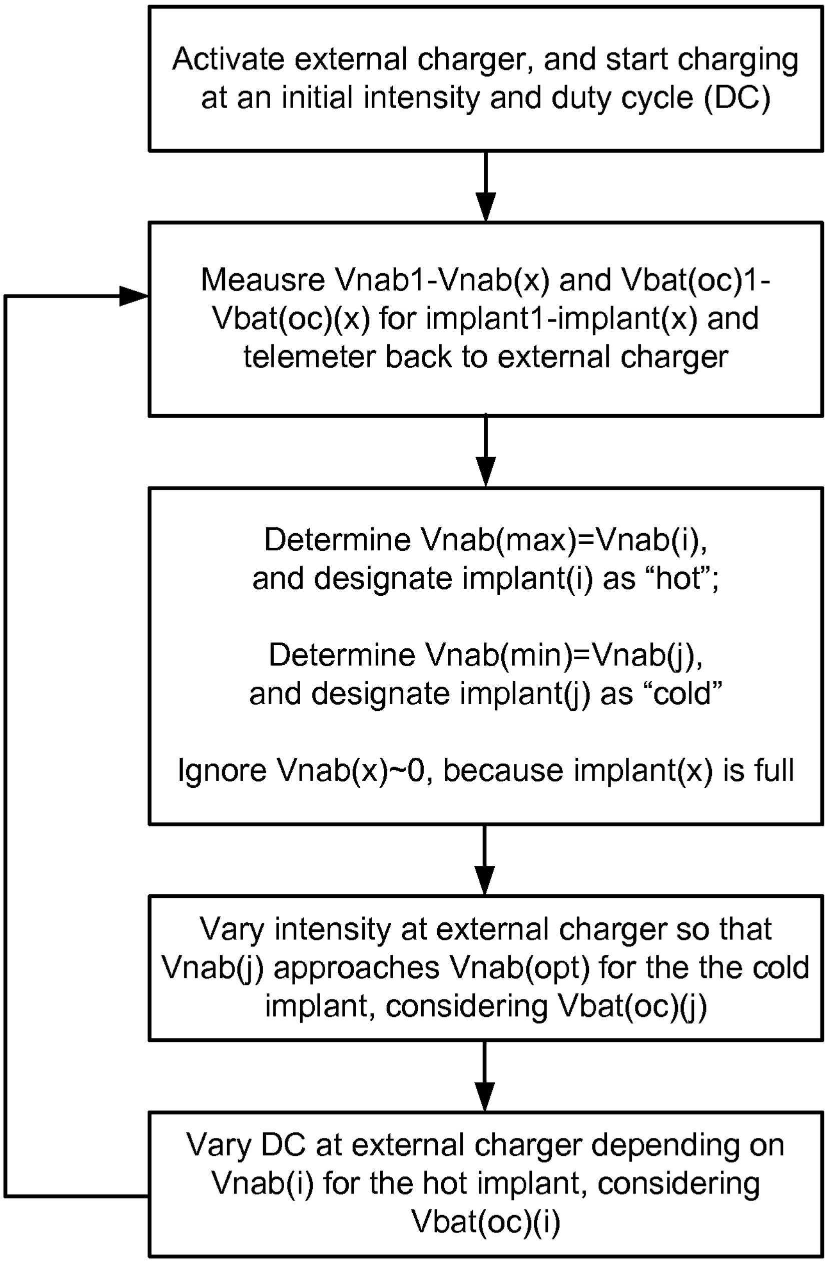
FIG. 15 illustrates a process for adjusting the power level and/or duty cycle at the external charger in accordance with the stored simulation parameters to optimize the charging of a plurality of implants.

When the parameters are received for each implant, the external charger 151 performs the steps shown in FIG. 15 to safely optimize charging for the implants. Like the similar single-implant method of FIG. 11, these steps can be embodied in a program executable within the charger’s microcontroller 300.

First, the external charger 151 is turned on (e.g., by the patient), and generates a magnetic charging field using an initial intensity level (i.e., an initial Iprim) and an initial duty cycle. Once again, the initial power and duty cycle values are not important as they will be changed in accordance with the disclosed technique as charging progresses, although they can be set to initial gross values during an alignment period similar to that already discussed.

Periodically during charging, the battery voltage (Vbat (oc)) and the voltage across the charging circuitry 170 (Vnab) are measured at each of the ‘x’ implants 100, and are telemetered to the external charger 151 as was discussed with reference to FIG. 14. Because multiple implants will be transmitting their values, it may be desirable to increase the frequency of transmissions so that the total time to report the implants' parameters is not too long.

Figure 4:
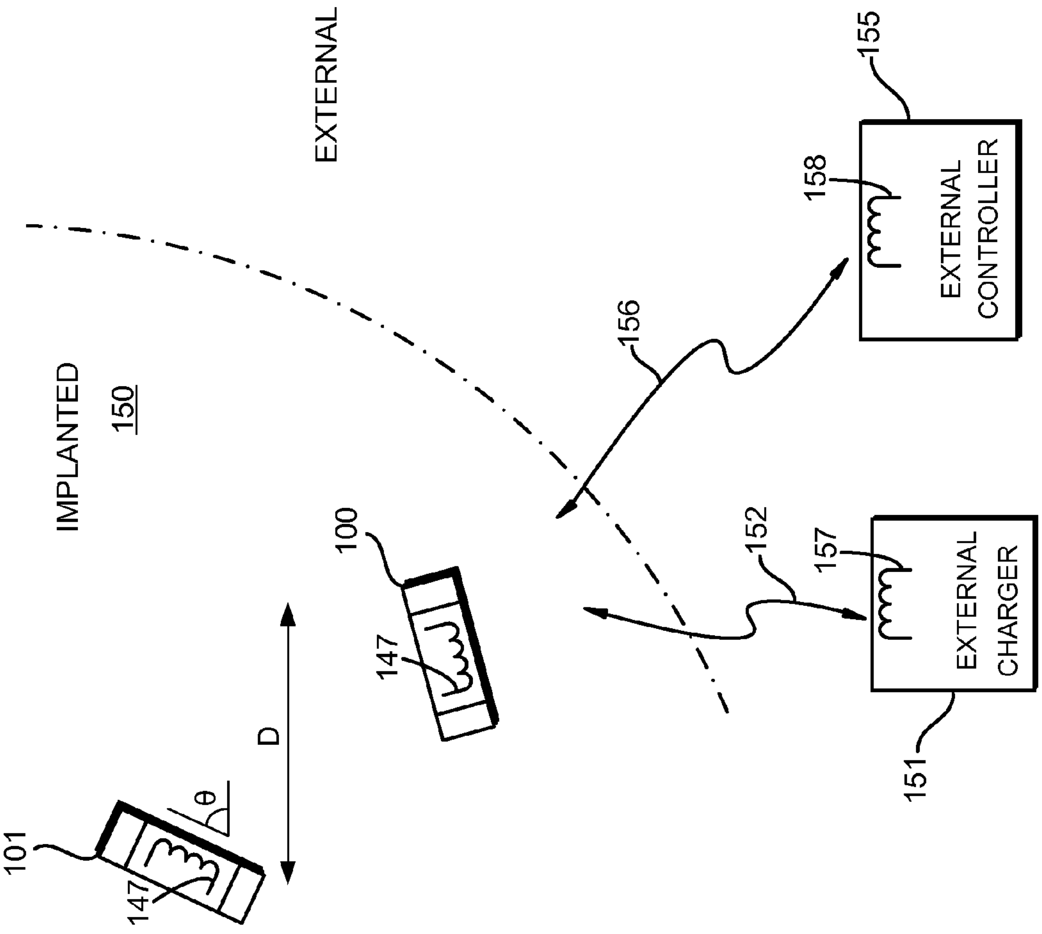
FIG. 4 illustrates duty cycling the power at the external charger to control implant temperature in accordance with the prior art.

Once the parameters for each implant have been reported, the Vnab values for each are compared to determine a maximum Vnab and a minimum Vnab, with the goal of designating a "hot" implant and a "cold" implant. Higher values of Vnab correspond to higher levels of wasted heat, which indicates higher coupling with the external charger 151. For example, and referring to FIG. 4, Vnab values reported from microstimulator 100 would be higher than for microstimulator 101 because of microstimulator 100's higher coupling to the external charger 151.

Therefore, the implant (implant(i)) with the highest Vnab (Vnab(max)=Vnab(i)) has the highest coupling with the external charger 151 and is most at risk to overheat; it is therefore designated as the "hot" implant. By contrast, the implant (implant(j)) with the lowest Vnab (Vnab(min)=Vnab (j)) has the lowest coupling with the external charger 151 and will likely be the slowest to charge; it is designated as the "cold" implant. Implants reporting very low Vnab values of essentially 0V are ignored, because the batteries in such implants are already fully charged, and hence are removed from analysis and optimization provided by FIG. 15, as will be explained further below. Of course, which implants are considered "hot" or "cold" at any given time may change over time during a charging session.

Once the hot and cold implants are determined, the intensity and duty cycle of the magnetic charging field are optimized at the external charger to ensure that no implant overheats, while still attempting to charge all implants efficiently. To quickly summarize, the cold implant(j) at any given time is used to set the intensity, while the hot implant(i) at any given time is used to set the duty cycle.

Because the currently-designated cold implant (implant(j)) will generally take the longest to charge, the intensity (Iprim) of the magnetic charging field is varied to approach a value for the average battery current Ibat(avg)(opt) that will charge the battery in implant(j) the quickest. As discussed earlier, that optimal current corresponds to Vnab(opt) (see, e.g., FIG. 8), and so the intensity is changed to try and move Vnab(j) toward Vnab(opt), with the intensity increased if Vnab(j)<Vnab(opt) and decreased if Vnab(j)>Vnab(opt). As discussed earlier, Vnab(opt) may vary depending on the reported battery voltage, Vbat(oc)(j), and so this parameter can be considered at this point in the process if necessary.

In the single-implant embodiment discussed earlier, the next step would be to choose a duty cycle for the external charger 151 that would maximize charging of the cold implant (implant (j)) by choosing a duty cycle that would allow implant(j) to heat up to the power dissipation limit (e.g., 32 mW/4° C.). However, this is not advisable when multiple implants are present: if currently-designated "cold" implant (j) is optimized to the power dissipation limit, currently-designated "hot" implant(i) would exceed that limit and overheat. Instead, the duty cycle is chosen to ensure that the "hot" implant (implant(i)) does not exceed the power dissipation limit. (Again, the duty cycle for "hot" implant(i) can be chosen with consideration to the hot implant(i)'s battery voltage, Vbat(oc)(i), if necessary). The result is that the "hot" implant will be allowed to approach but not exceed the power dissipation limitation, while the "cold" implant is charged with an optimally fast current, although with a duty cycle that would otherwise be less than optimal.

Other of the 'x' implants which are not the "hot" or "cold" implants(i) or (j) would be charged under non-optimal conditions compared to individual charging conditions, but conditions that nonetheless are safe from a heating perspective. That is, such other implants would be charged with battery currents lower than their ideal currents Ibat(avg)(opt) and with lower duty cycles than they could otherwise handle if optimized individually.

As mentioned briefly above, it is preferred to not consider at the external charger 151 data for any implants whose batteries have already been fully charged ("full implants" for short). Accordingly, it is preferred that full implants recognize when their batteries are at capacity; decouple themselves from receiving further power; and indicate such full capacity to the external charger 151 so that they can be discluded from the analysis and optimization routine of FIG. 15. This can occur in one example by having full implants actively detune themselves from the frequency of the magnetic charging field. Such active detuning can occur by either disconnecting or shorting the coil 147 or its tuning capacitor 162 (see FIG. 5A), which changes the resonant frequency of the L-C (tank) circuit formed by those two components. With the full implant so detuned, the L-C tank circuit will no longer resonate in response to the magnetic charging field, such that Vcoil (and consequently Vna and Vnab) are essentially zero, or are below some preset minimal limit. In effect, no power is being coupled to the full implant, its battery will not be further charged, and it is not at risk of overheating. Accordingly, when this negligible Vnab value is reported for a full implant, the external charger 151 can know to disclude it from the hot/cold analysis, and any further optimization of the intensity or duty cycle of the magnetic charging field.

Figure 16:
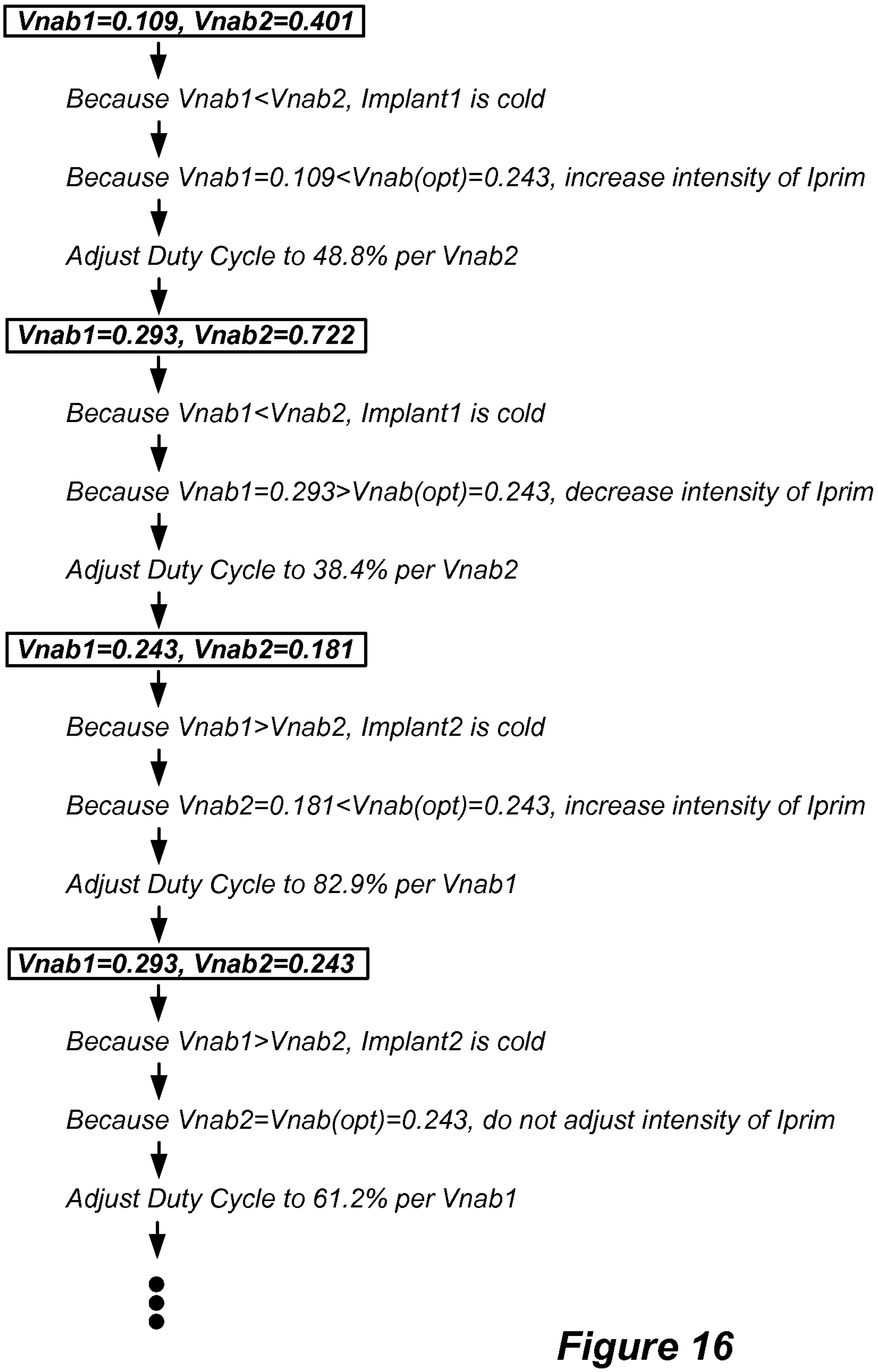
FIG. 16 illustrates an example of the charging of two implants in accordance with the process of FIG. 15.

An example illustrating the operation of the charging process of FIG. 15 is illustrated in FIG. 16, which for simplicity assumes a two-implant system, implant(1) and implant(2). For further simplicity, it is assumed that the open-circuit battery voltage in each of implants(1) and (2) equals 3.1V, to allow the reader easy reference to the values tabulated and stored in the external charger 151 in FIG. 13.

Suppose during charging that implants(1) and (2) report Vnab1 and 2 values of 0.109 and 0.401 respectively to the external charger 151, as shown at the top of FIG. 16. The smaller value for Vnab1 indicates lower coupling between implant1 and the external charger 151, perhaps because implant1 is farther away. Implant1 is therefore deemed the "cold" implant, and the intensity of the magnetic charging field (Iprim) is adjusted to try and optimize the battery charging current in implant1. Referencing the simulation data in FIG. 13, since the cold implant1's Vnab1=0.109 is lower than Vnab(opt)=0.243, Iprim is increased. The duty cycle is then adjusted to ensure that the "hot" implant2 will not exceed the power dissipation limits—i.e., will not heat more than 32 mW/4° C. Determining the correct duty cycle requires consulting Vnab2=0.401, which consulting memory 302 in FIG. 13 corresponds to a duty cycle of 48.8%. With these conditions, hot implant2 is constrained by the duty cycle not to exceed the power dissipation limit, and cold implant1 is optimized towards a battery charging current that will charge that implant the quickest.

Some time later, assume that Vnab1 and 2 values of 0.293 and 0.722 are reported as shown in FIG. 16. It is not surprising that these values are both larger, because it was previously decided in the last iteration to increase Iprim, and hence increase the intensity of the magnetic charge field. Once again, a comparison of Vnab1 and Vnab2 shows that implant1 is cold. However, because memory 302 indicates Vnab1=0.293>Vnab(opt)=0.243, optimizing the battery charging current in cold implant1 requires decreasing Iprim. Then, per memory 302, the duty cycle is set per Vnab2=0.722 to 38.4%.

Some time later, assume that Vnab1 and 2 values of 0.243 and 0.181 are reported as shown in FIG. 16. Because Vnab1>Vnab2, implant2 is now cold. This switch in coupling might have occurred for example because the patient has moved the external charger 151 closer to implant1 and further from implant2. Regardless of the reasons for the change, a benefit of the disclosed technique is its ability to handle such changes in coupling during a charging session. Because Vnab2=0.181<Vnab(opt)=0.243, optimizing the battery charging current in cold implant2 requires increasing Iprim. Then, the duty cycle is set per Vnab1=0.243 to 82.9%.

Some time later, assume that Vnab1 and 2 values of 0.293 and 0.243 are reported as shown in FIG. 16. It is not surprising that these values are both larger, because Iprim had been increased in the last iteration. A comparison of Vnab1 and Vnab2 shows that implant2 is still cold. However, because Vnab2=0.243=Vnab(opt), Iprim is not adjusted. However, the duty cycle for hot implant1 is set per Vnab1=0.293 to 61.2%.

It should be understood that various parameters (e.g., Vnab (opt); a DC corresponding to a particular Vnab) can be interpolated or extrapolated from the simulation 200, and are therefore not necessarily constrained to actual values appearing in the simulation. However, such interpolation was not shown to keep discussion of the technique simple.

Many of the parameters determined herein (e.g., Vnab (opt)) result from the simulation 200, which simulation provides a convenient expedient for understanding the external charger/implant system. However, not all implementations will require the use of a simulation. Instead, empirical data, experimental models, direct analytical tools, or values chosen by other means, could be used depending upon consideration of factors deemed important by the designer.

The disclosed technique limits the total power dissipated by the implant. However, the technique can be constrained to control heating at only a portion of the implant. For example, in larger implants or implants with low heat conductivity, the technique can be employed to limit the local heating at any section of the implant. In such an application, the technique can use a parameter (perhaps different from Vnab) indicative of heating to that section, and limiting heating of that particular section to tolerable limits. Thus, this modification to the technique would only consider power dissipated as heat in the relevant section of the device.

Vnab is used in this disclosure as the measure indicative of excess power dissipation. However, other parameters from the implant indicative of incoming power or power dissipated in heat and which can be used to control that power can also be used, such as total power delivered to the battery, ripple of the coil voltage, ripple of the rectified voltage, on time of the rectifying circuit, duty cycle of the rectifying circuit, etc. Of course, these parameters could be measured or inferred in the implant in different ways.

Even though the technique describes the periodic measurement of parameters in the implant during a charging session, and periodic adjustment of the magnetic charging field, "periodic" should not be understood as necessarily taking such actions at set intervals. Instead, "periodic" should be understood as taking a plurality of such actions over time, even if not at set intervals.

While the inventions disclosed have been described by means of specific embodiments and applications thereof, numerous modifications and variations could be made thereto by those skilled in the art without departing from the literal and equivalent scope of the inventions set forth in the claims.

What is claimed is:

1. A method for charging batteries in a plurality of implantable medical devices (IMDs), comprising:

(a) generating a magnetic charging field during a charging session using an external charger to simultaneously charge the batteries in the plurality of IMDs;

(b) determining, by the external charger, a first of the IMDs having a highest coupling to the external charger, and a second of the IMDs having a lowest coupling to the external charger; and (c) adjusting, by the external charger and based on at least one parameter of the determined first and second IMDs, the magnetic charging field during the charging session to maximize a speed of charging of the second IMD and to limit a power dissipation of the first IMD in accordance with a maximum power dissipation limit.

2. The method of claim 1, wherein adjusting the magnetic charging field to maximize the speed of charging of the second IMD comprises adjusting an intensity of the magnetic charging field, and wherein adjusting the magnetic charging field to limit the power dissipation of the first IMD comprises adjusting a duty cycle of the magnetic charging field.

3. The method of claim 2, wherein the external charger comprises a coil configured to generate the magnetic charging field, and wherein adjusting the intensity of the magnetic charging field comprises adjusting a current in the coil.

4. The method of claim 1, wherein determining the first and second IMDs comprises ignoring any of the plurality of IMDs whose battery is fully charged.

5. The method of claim 1, further comprising: (d) repeating steps (b) and (c) periodically during the charging session.

6. The method of claim 1, wherein determining the first and second IMDs comprises assessing the at least one parameter for each of the IMDs during the charging session.

7. The method of claim 6, wherein the at least one parameter for each IMD is indicative of a coupling between the external charger and that IMD.

8. The method of claim 7, wherein the magnetic charging field is further adjusted in accordance with a voltage of the battery in at least one of the first and second IMDs.

9. The method of claim 6, wherein the at least one parameter for each IMD is measured at that IMD, and wherein the at least one parameter is telemetered from each IMD to the external device during the charging session.

10. The method of claim 9, wherein the magnetic charging field is duty cycled, and wherein the at least one parameter for the IMDs are telemetered during one or more off periods in the duty cycle.

11. The method of claim 6, wherein the magnetic charging field induces a battery charging current in each IMD, and wherein the at least one parameter for each IMD is indicative of the battery charging current in that IMD.

12. The method of claim 11, wherein the at least one parameter comprises a voltage across circuitry in line with the battery charging current.

13. The method of claim 6, wherein determining the first and second IMDs comprises assessing a largest and smallest of the at least one parameter for each IMD.

14. The method of claim 6, wherein the external charger comprises data, and wherein the at least one parameter for the first and second IMDs are compared to the data to determine how to adjust the magnetic charging field.

15. The method of claim 14, wherein the data comprises an optimal value for the at least one parameter.

16. The method of claim 15, wherein the magnetic charging field is adjusted by adjusting an intensity of the magnetic charging field to bring the at least one parameter of the second IMD closer to the optimal value.

17. The method of claim 14, wherein the data relates the at least one parameter with a duty cycle that limits the power dissipation of the IMDs to the maximum power dissipation limit, and wherein the magnetic charging field is adjusted by adjusting a duty cycle of the magnetic charging field as determined from the data using the at least one parameter for the first IMD.

18. A method for charging batteries in a plurality of implantable medical devices (IMDs), comprising:

(a) generating a magnetic charging field during a charging session using an external charger to simultaneously charge the batteries in the plurality of IMDs;

(b) providing at the external charger at least one parameter indicative of a coupling between the external charger and each IMD during the charging session;

(c) determining, by the external charger, a first of the parameters corresponding to a first of the IMDs having a highest coupling to the external charger, and a second of the parameters corresponding to a second of the IMDs having a lowest coupling to the external charger; and (d) adjusting, by the external charger and based on the determined first and second parameters, the magnetic charging field during the charging session.

19. The method of claim 18, wherein adjusting the magnetic charging field comprises adjusting an intensity and a duty cycle of the magnetic charging field.

20. The method of claim 19, wherein the external charger comprises a coil configured to generate the magnetic charging field, and wherein adjusting the intensity of the magnetic charging field comprises adjusting a current in the coil.

21. The method of claim 19, wherein the intensity is adjusted in accordance with the first parameter, and wherein the duty cycle is adjusted in accordance with the second parameter.

22. The method of claim 18, wherein determining the first and second parameters comprises ignoring the at least one parameter corresponding to any of the IMDs whose battery is fully charged.

23. The method of claim 18, further comprising: (e) repeating steps (b) through (d) periodically during the charging session.

24. The method of claim 18, wherein the magnetic charging field is adjusted in accordance with the first parameter and the second parameter, and one or more of a battery voltage of the first IMD and the second 1 MB.

25. The method of claim 18, wherein the at least one parameter for each 1 MB is measured at that IMD, and wherein the at least one parameter is telemetered from each 1 MB to the external device during the charging session.

26. The method of claim 25, wherein the magnetic charging field is duty cycled, and wherein the at least one parameter for the IMDs are telemetered during one or more off periods in the duty cycle.

27. The method of claim 18, wherein the magnetic charging field induces a battery charging current in each IMD, and wherein the at least one parameter for each IMD is indicative of the battery charging current in that IMD.

28. The method of claim 27, wherein the at least one parameter comprises a voltage across circuitry in line with the battery charging current.

29. The method of claim 18, wherein determining the first and second parameters comprises assessing a largest and smallest of the at least one parameter for each IMD.

30. The method of claim 18, wherein the external charger comprises data, and wherein the first and second parameters are compared to the data to determine how to adjust the magnetic charging field.

31. The method of claim 30, wherein the data comprises an optimal value for the at least one parameter.

32. The method of claim 31, wherein the magnetic charging field is adjusted by adjusting an intensity of the magnetic charging field to bring the second parameter closer to the optimal value.

33. The method of claim 30, wherein the data relates the at least one parameter with a duty cycle that limits a power dissipation of the IMDs to a maximum power dissipation limit, and wherein the magnetic charging field is adjusted by adjusting a duty cycle of the magnetic charging field as determined from the data using the first parameter.

* * * * *